US009034356B2

(12) United States Patent
Shimp et al.

(10) Patent No.: US 9,034,356 B2
(45) Date of Patent: May 19, 2015

(54) POROUS OSTEOIMPLANT

(75) Inventors: Lawrence A. Shimp, Morganville, NJ (US); John Winterbottom, Jackson, NJ (US); David R. Kaes, Toms River, NJ (US); Ryan M. Belaney, Oakland, TN (US); Subhabrata Bhattacharyya, Brooklyn, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1425 days.

(21) Appl. No.: 11/625,086

(22) Filed: Jan. 19, 2007

(65) Prior Publication Data

US 2008/0069852 A1 Mar. 20, 2008

Related U.S. Application Data

(60) Provisional application No. 60/760,752, filed on Jan. 19, 2006, provisional application No. 60/760,239, filed on Jan. 19, 2006.

(51) Int. Cl.
| | |
|---|---|
| *A61L 27/56* | (2006.01) |
| *A61L 27/44* | (2006.01) |
| *A61L 27/46* | (2006.01) |
| *A61F 2/28* | (2006.01) |
| *A61F 2/30* | (2006.01) |

(52) U.S. Cl.
CPC . *A61L 27/56* (2013.01); *A61F 2/28* (2013.01); *A61F 2002/30062* (2013.01); *A61F 2002/30677* (2013.01); *A61F 2210/0004* (2013.01); *A61F 2310/00293* (2013.01); *A61F 2310/00365* (2013.01); *A61L 27/446* (2013.01); *A61L 27/46* (2013.01); *A61F 2310/00359* (2013.01)

(58) Field of Classification Search
USPC .................................. 424/423, 426
See application file for complete search history.

(56) References Cited

U.S. PATENT DOCUMENTS

| | | | |
|---|---|---|---|
| 3,892,649 A | 7/1975 | Phillips et al. | |
| 3,919,773 A | 11/1975 | Freeman | |
| 3,949,073 A | 4/1976 | Daniels et al. | |
| 4,183,874 A | 1/1980 | Fan et al. | |
| 4,551,156 A | 11/1985 | Li | |
| 4,595,713 A | 6/1986 | St. John | |
| 4,637,931 A | 1/1987 | Schmitz | |
| 4,638,045 A | 1/1987 | Kohn et al. | |
| 4,645,503 A | 2/1987 | Lin et al. | |
| 4,655,777 A | 4/1987 | Dunn et al. | |
| 4,743,259 A | 5/1988 | Bolander et al. | |
| 4,783,504 A | 11/1988 | St. Clair et al. | |
| 4,806,621 A | 2/1989 | Kohn et al. | |
| 4,880,610 A | 11/1989 | Constantz | |
| 4,882,149 A | 11/1989 | Spector | |
| RE33,161 E | 2/1990 | Brown et al. | |
| 4,902,296 A | 2/1990 | Bolander et al. | |
| RE33,221 E | 5/1990 | Brown et al. | |
| 4,946,929 A | 8/1990 | d'Amore et al. | |
| 5,010,167 A | 4/1991 | Ron et al. | |
| 5,019,379 A | 5/1991 | Domb et al. | |
| 5,034,059 A | 7/1991 | Constantz | |
| 5,047,031 A | 9/1991 | Constantz | |
| 5,053,212 A | 10/1991 | Constantz | |
| 5,129,905 A | 7/1992 | Constantz | |
| 5,133,755 A | 7/1992 | Brekke | |
| 5,149,368 A | 9/1992 | Liu et al. | |
| 5,160,674 A | 11/1992 | Colton et al. | |
| 5,162,445 A | 11/1992 | Powers et al. | |
| 5,246,782 A | 9/1993 | Kennedy et al. | |
| 5,262,166 A | 11/1993 | Liu et al. | |
| 5,262,461 A | 11/1993 | Serizawa et al. | |
| 5,268,178 A * | 12/1993 | Calhoun et al. | 424/426 |
| 5,290,555 A | 3/1994 | Gurthauser et al. | |
| 5,290,558 A | 3/1994 | O'Leary et al. | |
| 5,324,519 A | 6/1994 | Dunn et al. | |
| 5,333,626 A | 8/1994 | Morse et al. | |
| 5,336,264 A | 8/1994 | Constanz | |
| 5,340,614 A | 8/1994 | Perman et al. | |
| 5,352,715 A | 10/1994 | Wallace et al. | |
| 5,366,508 A | 11/1994 | Brekke | |
| 5,399,665 A | 3/1995 | Barrera et al. | |

(Continued)

FOREIGN PATENT DOCUMENTS

| | | |
|---|---|---|
| DE | 3716302 | 11/1988 |
| EP | 0 413 492 | 2/1991 |

(Continued)

OTHER PUBLICATIONS

Metsger et al, Tricalcium Phosphate Ceramic—a Resorbable Bone Implant, Journal of the American Dental Association, vol. 105, Issue 6, Abs.*
Popov et al, Laser Stereolithography and Supercritical Fluid Processing for Custom-Designed Implant Fabrication, Journal of Materials Science: Materials in Medicine 15, 2004, 123-128.*
Arora et al, Macromolecules, 1998, 32, 4614-4620.*
Dietmar W. Hutmacher, Biomaterials, 2000, 21, 2529-2543.*

(Continued)

*Primary Examiner* — Misook Yu
*Assistant Examiner* — Kauser Akhoon
(74) *Attorney, Agent, or Firm* — Sorell Lenna & Schmidt LLP

(57) ABSTRACT

The invention is directed toward porous composites for application to a bone defect site to promote new bone growth. The inventive porous composites comprise a biocompatible polymer and a plurality of particles of bone-derived material, inorganic material, bone substitute material or composite material. In certain embodiments, the porous composites are prepared using a method that includes a supercritical fluid (e.g., supercritical carbon dioxide) treatment. The invention also discloses methods of using these composites as bone void fillers.

29 Claims, 4 Drawing Sheets

(56) References Cited

U.S. PATENT DOCUMENTS

| | | |
|---|---|---|
| 5,417,975 A | 5/1995 | Lussi et al. |
| 5,462,722 A | 10/1995 | Liu et al. |
| 5,468,544 A | 11/1995 | Marcolongo et al. |
| 5,507,813 A | 4/1996 | Dowd et al. |
| 5,512,600 A | 4/1996 | Mikos et al. |
| 5,513,662 A | 5/1996 | Morse et al. |
| 5,514,378 A | 5/1996 | Mikos et al. |
| 5,525,148 A | 6/1996 | Chow et al. |
| 5,542,973 A | 8/1996 | Chow et al. |
| 5,552,454 A | 9/1996 | Kretschmann et al. |
| 5,573,771 A | 11/1996 | Geistlich et al. |
| 5,605,713 A | 2/1997 | Boltong |
| 5,606,000 A | 2/1997 | Jadhav et al. |
| 5,624,463 A | 4/1997 | Stone et al. |
| 5,626,861 A | 5/1997 | Laurencin et al. |
| 5,641,502 A | 6/1997 | Skalla et al. |
| 5,650,176 A | 7/1997 | Lee et al. |
| 5,679,723 A | 10/1997 | Cooper et al. |
| 5,696,175 A | 12/1997 | Mikos et al. |
| 5,707,962 A | 1/1998 | Chen et al. |
| 5,714,159 A | 2/1998 | Shalaby |
| 5,716,404 A | 2/1998 | Vacanti et al. |
| 5,716,413 A | 2/1998 | Walter et al. |
| 5,717,006 A | 2/1998 | Daculsi et al. |
| 5,736,160 A | 4/1998 | Ringeisen et al. |
| 5,736,372 A | 4/1998 | Vacanti et al. |
| 5,766,618 A | 6/1998 | Laurencin et al. |
| 5,766,637 A | 6/1998 | Shine et al. |
| 5,770,417 A | 6/1998 | Vacanti et al. |
| 5,804,178 A | 9/1998 | Vacanti et al. |
| 5,817,328 A | 10/1998 | Gresser et al. |
| 5,824,359 A * | 10/1998 | Khan et al. ............... 427/2.3 |
| 5,837,752 A | 11/1998 | Shastri et al. |
| 5,846,484 A | 12/1998 | Scarborough et al. |
| 5,846,951 A | 12/1998 | Gregoriadis |
| 5,863,297 A | 1/1999 | Walter et al. |
| 5,899,939 A | 5/1999 | Boyce et al. |
| 5,902,599 A | 5/1999 | Anseth et al. |
| 5,935,594 A | 8/1999 | Ringeisen et al. |
| 5,948,386 A | 9/1999 | Katti et al. |
| 5,977,204 A | 11/1999 | Boyan et al. |
| 5,981,619 A | 11/1999 | Shikinami et al. |
| 6,001,394 A | 12/1999 | Daculsi et al. |
| 6,002,065 A | 12/1999 | Constantz et al. |
| 6,027,744 A | 2/2000 | Vacanti et al. |
| 6,030,635 A | 2/2000 | Gertzman et al. |
| 6,033,852 A | 3/2000 | Andle et al. |
| 6,095,148 A | 8/2000 | Shastri et al. |
| 6,117,456 A | 9/2000 | Lee et al. |
| 6,119,028 A | 9/2000 | Schulman et al. |
| 6,123,727 A | 9/2000 | Vacanti et al. |
| 6,123,731 A | 9/2000 | Boyce et al. |
| 6,127,442 A | 10/2000 | Sulzbach et al. |
| 6,132,468 A | 10/2000 | Mansmann |
| 6,156,068 A | 12/2000 | Walter et al. |
| 6,165,486 A | 12/2000 | Marra et al. |
| 6,180,605 B1 | 1/2001 | Chen et al. |
| 6,180,606 B1 | 1/2001 | Chen et al. |
| 6,183,498 B1 | 2/2001 | Devore et al. |
| 6,203,573 B1 | 3/2001 | Walter et al. |
| 6,206,957 B1 | 3/2001 | Driessens et al. |
| 6,224,630 B1 | 5/2001 | Bao et al. |
| 6,294,041 B1 | 9/2001 | Boyce et al. |
| 6,294,187 B1 | 9/2001 | Boyce et al. |
| 6,328,990 B1 | 12/2001 | Ducheyne et al. |
| 6,332,779 B1 | 12/2001 | Boyce et al. |
| 6,340,477 B1 | 1/2002 | Anderson |
| 6,344,496 B1 | 2/2002 | Niederauer et al. |
| 6,352,667 B1 | 3/2002 | English |
| 6,376,573 B1 | 4/2002 | White et al. |
| 6,399,693 B1 | 6/2002 | Brennan et al. |
| 6,406,498 B1 | 6/2002 | Törmälä et al. |
| 6,413,539 B1 | 7/2002 | Shalaby |
| 6,414,050 B1 | 7/2002 | Howdle et al. |
| 6,419,945 B1 | 7/2002 | Gresser et al. |
| 6,432,436 B1 | 8/2002 | Gertzman et al. |
| 6,437,018 B1 | 8/2002 | Gertzman et al. |
| 6,440,444 B2 | 8/2002 | Boyce et al. |
| 6,441,073 B1 | 8/2002 | Tanaka et al. |
| 6,471,993 B1 | 10/2002 | Shastri et al. |
| 6,478,825 B1 | 11/2002 | Winterbottom et al. |
| 6,503,278 B1 | 1/2003 | Pohjonen et al. |
| 6,511,511 B1 | 1/2003 | Slivka et al. |
| 6,524,345 B1 | 2/2003 | Valimaa et al. |
| 6,579,532 B1 | 6/2003 | Mandel et al. |
| 6,583,232 B1 | 6/2003 | Brown |
| 6,670,407 B2 | 12/2003 | Howdle et al. |
| 6,673,286 B2 | 1/2004 | Shih et al. |
| 6,696,073 B2 | 2/2004 | Boyce et al. |
| RE38,522 E | 5/2004 | Gertzman et al. |
| 6,747,121 B2 | 6/2004 | Gogolewski et al. |
| 6,867,240 B2 | 3/2005 | Ma et al. |
| 6,911,212 B2 | 6/2005 | Gertzman et al. |
| 6,933,328 B2 | 8/2005 | Schacht |
| 7,004,974 B1 | 2/2006 | Larsson et al. |
| 7,012,106 B2 | 3/2006 | Yuan et al. |
| 7,122,057 B2 | 10/2006 | Beam et al. |
| 2001/0014831 A1 | 8/2001 | Scarborough |
| 2001/0051833 A1 | 12/2001 | Walter et al. |
| 2002/0035401 A1 | 3/2002 | Boyce et al. |
| 2002/0098222 A1 | 7/2002 | Wironen et al. |
| 2003/0009235 A1* | 1/2003 | Manrique et al. ......... 623/23.63 |
| 2003/0036800 A1 | 2/2003 | Meredith |
| 2003/0039676 A1 | 2/2003 | Boyce et al. |
| 2003/0045942 A1 | 3/2003 | Lai et al. |
| 2003/0065400 A1 | 4/2003 | Beam et al. |
| 2003/0077311 A1 | 4/2003 | Vyakarnam et al. |
| 2003/0114552 A1 | 6/2003 | Schacht |
| 2003/0114936 A1* | 6/2003 | Sherwood et al. ......... 623/23.58 |
| 2003/0144743 A1 | 7/2003 | Edwards et al. |
| 2003/0180344 A1 | 9/2003 | Wise et al. |
| 2003/0206937 A1 | 11/2003 | Gertzman et al. |
| 2003/0236573 A1 | 12/2003 | Evans et al. |
| 2004/0006153 A1 | 1/2004 | Seppala et al. |
| 2004/0010048 A1 | 1/2004 | Evans et al. |
| 2004/0024457 A1 | 2/2004 | Boyce et al. |
| 2004/0034434 A1 | 2/2004 | Evans et al. |
| 2004/0064193 A1 | 4/2004 | Evans et al. |
| 2004/0127987 A1 | 7/2004 | Evans et al. |
| 2004/0137032 A1* | 7/2004 | Wang ........................ 424/423 |
| 2004/0138758 A1 | 7/2004 | Evans et al. |
| 2004/0146543 A1 | 7/2004 | Shimp et al. |
| 2004/0197373 A1 | 10/2004 | Gertzman et al. |
| 2004/0228898 A1 | 11/2004 | Ross et al. |
| 2004/0253290 A1 | 12/2004 | Kim et al. |
| 2005/0008620 A1 | 1/2005 | Shimp et al. |
| 2005/0008672 A1* | 1/2005 | Winterbottom et al. ...... 424/423 |
| 2005/0013793 A1 | 1/2005 | Beckman et al. |
| 2005/0027033 A1 | 2/2005 | Knaack et al. |
| 2005/0042253 A1 | 2/2005 | Farrar et al. |
| 2005/0084533 A1 | 4/2005 | Howdle et al. |
| 2005/0100578 A1 | 5/2005 | Schmid et al. |
| 2005/0107887 A1 | 5/2005 | Knothe Tate et al. |
| 2005/0129726 A1 | 6/2005 | Liebschner |
| 2005/0216321 A1 | 9/2005 | Lyu et al. |
| 2005/0238683 A1 | 10/2005 | Adhikari et al. |
| 2005/0249773 A1 | 11/2005 | Maspero et al. |
| 2005/0251266 A1 | 11/2005 | Maspero et al. |
| 2005/0251267 A1 | 11/2005 | Winterbottom et al. |
| 2005/0281856 A1 | 12/2005 | McGlohorn et al. |
| 2006/0067971 A1 | 3/2006 | Story et al. |
| 2006/0067973 A1 | 3/2006 | Schachter |
| 2006/0121087 A1 | 6/2006 | Williams et al. |
| 2006/0127442 A1 | 6/2006 | Helmus |
| 2006/0204581 A1 | 9/2006 | Gower et al. |
| 2006/0216323 A1 | 9/2006 | Knaack et al. |
| 2006/0263335 A1 | 11/2006 | France et al. |

FOREIGN PATENT DOCUMENTS

| | | |
|---|---|---|
| FR | 2364644 | 4/1978 |
| GB | 03/07011 | 3/2003 |
| WO | WO 8805312 A1 | 7/1988 |
| WO | WO-90/01342 | 8/1988 |

(56) References Cited

FOREIGN PATENT DOCUMENTS

| WO | WO 9012550 A1 | 11/1990 |
|---|---|---|
| WO | WO-91/09079 | 6/1991 |
| WO | WO 9526762 A1 | 10/1995 |
| WO | WO-97/10010 | 3/1997 |
| WO | WO-97/11725 | 4/1997 |
| WO | WO-98/18408 | 5/1998 |
| WO | WO-98/19718 | 5/1998 |
| WO | WO-98/51347 | 11/1998 |
| WO | WO-98/53768 | 12/1998 |
| WO | WO-00/01426 | 1/2000 |
| WO | WO-03/078508 | 9/2003 |
| WO | WO-2004/053112 | 12/2003 |
| WO | WO-2004/014452 | 2/2004 |
| WO | WO-2004/032988 | 4/2004 |
| WO | WO2004091435 | * 10/2004 |
| WO | WO-2006/045183 | 5/2006 |

OTHER PUBLICATIONS

MCA Services (http://www.mcaservices.co.uk/poresizedistribution.htm).*

PEG-6000 (http://www.kat-chem.hu/en/prod-bulletins/polietilenglikol-6000#).*

Reddi et al., "Biochemical Sequences in the Transformation of Normal Fibroblasts in Adolescent Rats", Proc. Natl. Acad. Sci. USA, 69:1601-5, 1972.

Lewandrowski et al., "Kinetics of cortical bone demineralization: Controlled demineralization—a new method for modifying cortical bone allografts", J. Biomed. Mater. Res., 31: 365-72, 1996.

Hurley et al., "Anorganic Bone—Chemistry, Anatomy, and Biological Reactions" Milit. Med., 101-4, 1957.

Kershaw, "Preparation of Anorganic Bone Grafting Material", Pharm. J., 6: 537, 1963.

de Wijn et al., "Grafting PMMA on Hydroxyapatite Powder Particles using Isocyanatoethylmethacrylate", Fifth World Biomaterials Congress, May 29-Jun. 2, 1996, Toronto, CA.

James et al., "Small changes in polymer chemistry have a large effect on the bone-implant interface: evaluation of a series of degreadable tyrosine-derived polycarbonates in bone defects", Biomaterials, 20: 2203-313, 1999.

Langer, "Biomaterials in drug delivery and tissue engineering: one laboratory's experience", Acc. Chem. Res., 33: 94, 2000.

Langer, "Selected advances in drug delivery and tissue engineering", J. Control Release, 62: 7, 1999.

Uhrich et al., "Polymeric systems for controlled drug release", Chem. Rev., 99: 3181, 1999.

Allcock et al., "Synthesis of poly (amino acid alkyl ester) phosphazenes", Macromolecules, 10: 824-30,. 1977.

Allcock et al., "Hydrolysis pathways for aminophosphazenes", Inorg. Chem., 21: 515-21, 1982.

Mikos et al., "Prevascularization of biodegradable polymer scaffolds for hepatocyte transplantation", Proc. ACS Div. of Polymer Mater., 66: 33, 1992.

Eggli et al., "Porous Hydroxyapatite and tricalcium phosphate cylinders with two different pore size ranges implanted in the cancellous bone of rabbits", Clin Orthop., 232: 127-38, 1987.

White et al., "Biomaterial aspects of Interpore 200 porous hydroxyapatite", Dental Cliical of N. Amer., 30: 49-67, 1986.

Klaitwatter et al., "Application of porous ceramics for the attachment of load bering orthopedic applications", J. Biomed. Mater. Res. Symp., 2: 161, 1971.

Murphy et al., "Salt Fusion: An Approach to Improve Pore Interconeectivity withing Tissue Engineering Scaffolds", Tissue Engineering, 8(1): 43-52, 2002.

Karageorgiou et al., "Porosity of 3D biomaterial scaffolds and osteogenesis", Biomaterials, 26: 5474-91, 2005.

Bohner et al., "Theoretical and experimental model to describe the injection of a polymethylmethacrylate cement into a porous structure", Biomaterials, 24: 2721-30, 2003.

Bohner et al., "Injectability of calcium phosphate pastes", Biomaterials, 26: 1553-63, 2005.

Giannitsios et al., "High Cement Viscosity Reduces Leakage Risk in Vertebroplasty", European Cells and Materials, 10(3): 54, 2005.

Vogt et al., "Fabrication of Highly Porous Scaffold Materials based on Functionalized Oligolactides and Preliminary Results on Their Use in Bone Tissue Engineering", European Cells and Materials, 4: 30-38, 2002.

Schmitz et al., "A Preliminary Study of the Osteogenic Potential of a Biodegradable Alloplastic-Osteoinductive Alloimplant", Clinical Orthopaedics and Related Research, 237: 245-55, 1988.

International Search Report for PCT/US03/39704, date of mailing Jun. 2, 2004.

Baker, Gregory L., http://www.cem.msu.edu/~gradoff/brochf/Baker.htm, printed Aug. 2002.

Bosch, P., "Bone Grafting with Fibrin Glue", Wiener Klinische Wochenschroft Supplementum, 93, No. 124, pp. 3-26, 1981.

Han, et al., "Synergistic Effects of Lecithin and Human DBM on Bone Induction in Nude Rats", Society for Biomaterials, 28th Annual Meeting Transactions, 2002 (abstract).

Hooper, et al., "Diphenolic Monomers Derived from the Natural Amino Acid α-L-Tyrosine: An Evaluation of Peptide Coupling Techniques", Journal of Bioactive and Compatible Polymers 10, 327-340 (1995).

Nazhat, S.N., et al., "Dynamic Mechanical Behaviour of Modified Hydroxyapatite Reinforced Polyethylene Composites", Fifth World Biomaterials Congress, p. 83, May 29-Jun. 2, 1996.

Satish Pulapura, et al., "Tyrosine-Derived Polycarbonates: Backbone-Modified "Pseudo"-Poly (Amino Acids) Designed for Biomedical Applications", Biopolymers 32, 411-417 (1992).

"Silane Coupling Agent", http://www.apr.co.kr/silaneen.htm, printed Aug. 7, 2002.

Simmons, D.M., et al., "Evaluation of collagen cross-linking techniques for the stabilization of tissue matrices", Biotechnol. Appl. Biochem. 17, 23-29 (1993).

Tangpasuthadol, Varawut, "Thermo-Mechanical Properties and Hydrolytic Degradation of Tyrosine-Derived Polymers for Use in Biomedical Applications", Ph.D. Dissertation, Rutgers, The State University of New Jersey, (Jan. 1999).

Whittaker, et al., "Matrix Metalloproteinases and their Inhibitors—Current Status and Future Challenges", Celltransmissions, 17, prior to Jun. 13, 2002.

Zhiyuan Zhong, et al., "Calcium methoxide initiated ring-opening polymerization of ε-caprolactone and L-lactide", Polymer Bulletin 46, 51-57 (2001).

Forssell et al., "Experimental Osteosynthesis with Liquid Ethyl Cyanacrylate Polymerized with Ultrasound", Arch. Orthop Trauma Surg, 103: 278-83, 1984.

Liu et al., "Covalent Bonding of PMMA, PBMA, and ply(HEMA) to Hydroxyapatite Particles", J. Biomed. Mater. Res., 40: 257-63, 1998.

International Search Report for PCT/US05/15426, mailed on Mar. 27, 2006.

International Search Report for PCT/US03/25417, mailed on Jul. 2, 2004.

Boesch, "Bone Grafting with Fibrin Glue" Wiener Klinische Wochenschrift, 93(124):3-26 (1981).

International Search Report for PCT/EP89/00893, mailed on Dec. 1, 1989.

International Search Report for PCT/FI96/00511, mailed on Jan. 11, 1997.

International Search Report for PCT/US07/01325, mailed on Nov. 2, 2007.

* cited by examiner

| Polymer | Samples (ratio) | Compression | | Hydration | Molding Method |
|---|---|---|---|---|---|
| | | N | Yield Stress (MPa) | | |
| Resomer 824 | Fibers (65/35) | 3 | 2.75 ± 0.5 * | 1 day | $SSCO_2$ |
| Resomer 824 | Fibers (65/35 with PEG | 3 | 2.42 ± 1.1 * | 1 day | $SSCO_2$ |

* stress at 20% strain.

Figure 3

POROUS OSTEOIMPLANT

RELATED APPLICATIONS

This application claims priority from Provisional Application No. 60/760,752 filed on Jan. 19, 2006 and entitled "Porous Bone Void Filler" and Provisional Application No. 60/760,239 filed on Jan. 19, 2006 and entitled "Bone Substitute Material". Each of the provisional applications is incorporated herein by reference in its entirety.

FIELD OF THE INVENTION

This invention pertains to porous osteoimplants.

BACKGROUND OF THE INVENTION

Bone is a composite material composed of impure hydroxyapatite, collagen, and a variety of non-collagenous proteins, as well as embedded and adherent cells. Bone can be processed into an implantable biomaterial, such as an allograft, for example, by removing the cells, leaving behind the extracellular matrix. The processed bone material can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's bone and may alternatively be processed into soft, moldable, or flowable demineralized bone materials that have the ability to induce a cellular healing response.

The use of bone grafts and bone substitute materials in orthopedic medicine is well known. While bone wounds can regenerate without the formation of scar tissue, fractures and other orthopedic injuries take a long time to heal, during which the bone is unable to support physiologic loading. Metal pins, screws, and meshes are frequently required to replace the mechanical functions of injured bone. However, metal is significantly stiffer than bone. Use of metal implants may result in decreased bone density around the implant site due to stress shielding. Furthermore, most metal implants are permanent and unable to participate in physiological remodeling.

Bone's cellular healing processes, using bone tissue formation by osteoblast cells coordinated with bone and graft resorption by osteoclast cells, permit bone grafts and certain bone substitute materials to remodel into endogenous bone that is almost indistinguishable from the original. However, the use of bone grafts is limited by the available shape and size of grafts and the desire to optimize both mechanical strength and degradation rate. Variations in bone size and shape among patients (and donors) also make bone grafts a less optimal substitute material. Bone substitute materials and bone chips are quickly remodeled but cannot immediately provide mechanical support. In contrast, cortical bone grafts can support physiological stresses but remodel slowly.

Methods have been developed for preparing composites (see, for example, U.S. Pat. Nos. 5,507,813; 5,899,939; 6,123,731; 6,294,041; 6,294,187; 6,332,779; 6,440,444; and 6,478,825, each of which is incorporated herein by reference) including allogenic bone for use in load bearing orthopedic applications. However, in some applications, it is desirable to increase the rate at which native tissue penetrates implanted material, while it may not be necessary that the material actually bear weight. In these applications, it is desirable to have an implantable material that is optimized for infiltration with less emphasis on mechanical strength.

SUMMARY OF THE INVENTION

The present invention is directed to new systems and strategies for bone repair. In particular, the present invention provides porous composites which, upon implantation, promote cellular infiltration from adjacent osseous tissues, thus accelerating the remodeling process. The inventive composites comprise a polymer, such as a biocompatible polymer, and a plurality of particles of inorganic material, bone-derived material, bone substitute material, or composite material. The present invention also provides methods that can be used for the preparation of such composites that involve a supercritical fluid (e.g., supercritical carbon dioxide) treatment. The invention also provides methods and kits for using the inventive porous materials.

More specifically, in one aspect, the present invention provides a porous composition comprising a plurality of particles comprising a bone-derived material, an inorganic material, a bone substitute material, or any combination thereof, and a biocompatible polymer.

In certain embodiments, the porous composite has a density of between about 1.6 g/cm$^3$ and about 0.05 g/cm$^3$. In some embodiments, the porous composite has a density of between about 1.1 g/cm$^3$ to about 0.07 g/cm$^3$. For example, the density may be less than about 1 g/cm$^3$, less than about 0.9 g/cm$^3$, less than about 0.8 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

In certain embodiments, the porous composite has a porosity of at least about 30%, at least about 50%, at least about 60%, at least about 70%, at least about 80%, at least about 90% or more than 90%. Porous compositions of the present invention may comprise pores or channels which, after implantation, can support the in-growth of cell and/or the formation or remodeling of bone. Alternatively or additionally, inventive porous composites may comprise latent pores that become actual pores after the composite is implanted in vivo.

In certain embodiments, the porous composite comprises at least some pores that result from a supercritical fluid treatment. For example, the supercritical fluid treatment may comprise the use of supercritical carbon dioxide.

The particles in the composite may have a variety of shapes including spheroidal, plate, fiber, cuboidal, sheet, rod, ellipsoidal, string, elongated, polyhedral, and mixtures thereof. The particles in the composite have an average size of about 10 to about 1000 microns in diameter, preferably an average size of about 20 to about 800 microns in diameter. In certain embodiments, the median size of the particles ranges from about 10 to about 1000 microns in diameter, preferably from about 20 to about 800 microns. Smaller or large particles may also be found in the composite. A particle size distribution of the particles with respect to a median value may be plus and minus about 90% or less, about 50% or less, or about 20% or less. In certain embodiments, at least about 60% of the particles have a median size of about 10 microns to about 1000 microns in their greatest dimension. In certain embodiments, at least about 60% of the particles have a median size of about 20 microns to about 800 microns in their greatest dimension.

The polymer used in preparing the inventive composite may be selected from monomers, pre-polymers, oligomers, polymers, cross-linked polymers, partially polymerized polymers, partially cross-linked polymers, and any combinations thereof. For example, the composite may include monomers, oligomers, and polymers. Exemplary polymers useful in the inventive composites include, but are not limited to, poly(lactide), poly(glycolide), poly(lactide-co-glycolide), poly(D,L-lactide-co-glycolide), poly(L-lactide-co-glycolide), poly(caprolactone), polyurethane, polycarbonates, polyarylates, poly(propylene fumarates), polyphosphazines, and combinations thereof.

In certain embodiments, the composite include particles of bone-derived material. The bone-derived material of such composites may include one or more of nondemineralized bone particles, demineralized bone particles, lightly demineralized bone particles, and deorganified bone particles. The bone-derived material may include one or more of cortical bone, cancellous bone, and cortico-cancellous bone. Also, the bone-derived material may include autogenous bone, allogenic bone, and xenogeneic bone. In certain embodiments, the composite includes an inorganic material (e.g., an inorganic ceramic) and/or a bone substitute material. Exemplary inorganic materials or bone substitute materials useful in the inventive composites include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, a-tricalcium phosphate, dicalcium phosphate, β-tricalcium phosphate, tetracalcium phosphate, amorphous calcium phosphate, octacalcium phosphate, BIOGLASS™, fluorapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium, sodium, potassium, etc.), and combinations and derivatives thereof. In certain embodiments, the particles themselves are composites that include one or more of an inorganic material, a bone substitute material, and a bone-derived material; and one or more of bovine serum albumin, collagen, an extracellular matrix component, a synthetic polymer, and a natural polymer. The composite may range from approximately 10% particles to about 95% particles by weight, for example, approximately 50% particles to approximately 80% particles by weight. In certain embodiments, the composite is approximately 50%, approximately 55%, approximately 60%, or approximately 65% particles by weight. The composite may also include other components. For example, the composite may further include one or more of an initiator, accelerator, catalyst, solvent, wetting agent, lubricating agent, labeling agent, plasticizer, radiopacifier, porogen, bioactive agent, biostatic agent, cell, polynucleotide, protein (e.g., bone morphogenic protein, cytokine, growth factor, aniogenic factor), pharmaceutical agent (e.g., anti-inflammatory agent, analgesic, antibiotic, etc.), and pharmaceutically acceptable excipient. In certain embodiments, the composite includes a plasticizer that softens the composite making it more pliable. An exemplary plasticizer is poly(ethylene glycol) (PEG) (e.g., PEG 8000, PEG 6000, PEG 4000). In certain embodiments, the composite includes a porogen that diffuses, dissolves, and/or degrades after implantation of the composite leaving a pore. The porogen may be a gas (e.g., carbon dioxide, nitrogen), liquid (e.g., water), or solid (e.g., crystalline salt). The porogen may be a water-soluble chemical compound such as a carbohydrate (e.g., poly(dextrose), dextran), salt, polymer (e.g., polyvinyl pyrrolidone), protein (e.g., gelatin), pharmaceutical agent (e.g., antibiotics), small molecule, etc.

In certain embodiments, the porous composite has a shape selected from the group consisting of morsels, cylinder, block, wedge, and sheet.

In certain embodiments, the porous composite is configured for the repair of a simple fracture, compound fracture or non-union; as an external fixation device or internal fixation device; for joint reconstruction, arthrodesis, arthroplasty or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones or metatarsal bones.

In another aspect, the present invention provides an osteoimplant comprising an inventive porous composite. The present invention also provides an osteoimplant comprising an osteoimplant at least partially coated with an inventive porous composite.

In still another aspect, the present invention provides a method of preparing a porous composite comprising steps of providing a plurality of particles comprising a bone-derived material, an inorganic material, a bone substitute material, a composite material, or any combination thereof, providing a biocompatible polymer; mixing the particles and biocompatible polymer to obtain a mixture; and submitting the mixture to a supercritical fluid treatment to obtain the porous composite. Submitting the mixture to supercritical fluid treatment to obtain the porous composite may comprise steps of: contacting the mixture with a supercritical fluid for a period of time, and returning the supercritical fluid to a non-supercritical state. Returning the supercritical fluid to a non-supercritical fluid may comprise reducing the supercritical fluid temperature, the supercritical fluid pressure, or both reducing both the supercritical fluid temperature and pressure. In certain embodiments, returning the supercritical fluid to a non-supercritical state comprises submitting the supercritical fluid to a rapid or explosive decompression. In certain embodiments, the supercritical fluid is supercritical carbon dioxide ($SCCO_2$).

In yet another aspect, the present invention provides a method of treating a bone in a subject comprising administering an inventive porous composite or inventive osteoimplant to a subject in need thereof. The subject is generally a vertebrate, e.g., a mammal including a human. The subject may be suffering from a bone fracture or a bone defect. A inventive porous composite or osteoimplant may be administered for the treatment of a genetic disease, a congenital abnormality, a fracture, an iatrogenic defect, a bone cancer, a bone metastasis, an inflammatory disease, an autoimmune disease, a metabolic disease, or a degenerative bone disease.

In yet another aspect, the present invention provides kits for the treatment of bone. Kits comprise a porous composite (or osteoimplant) described herein, wherein the composite (or osteoimplant) is sterilely packaged. Various amounts of the composite may be packaged in a kit. The amount of composite packaged in a kit may depend on the procedure being performed on the subject. In certain embodiments, multiple individually packaged amounts of composite are included in one kit. Kits may further comprise a solvent or pharmaceutically acceptable excipient and/or instructions for administering the composite or osteoimplant.

These and other objects, advantages and features of the present invention will become apparent to those of ordinary skill in the art having read the following detailed description of the preferred embodiments.

BRIEF DESCRIPTION OF THE DRAWING

FIG. 3 is a table comparing the properties of various composites produced according to exemplary embodiments of the invention.

DEFINITIONS

Figure 1:
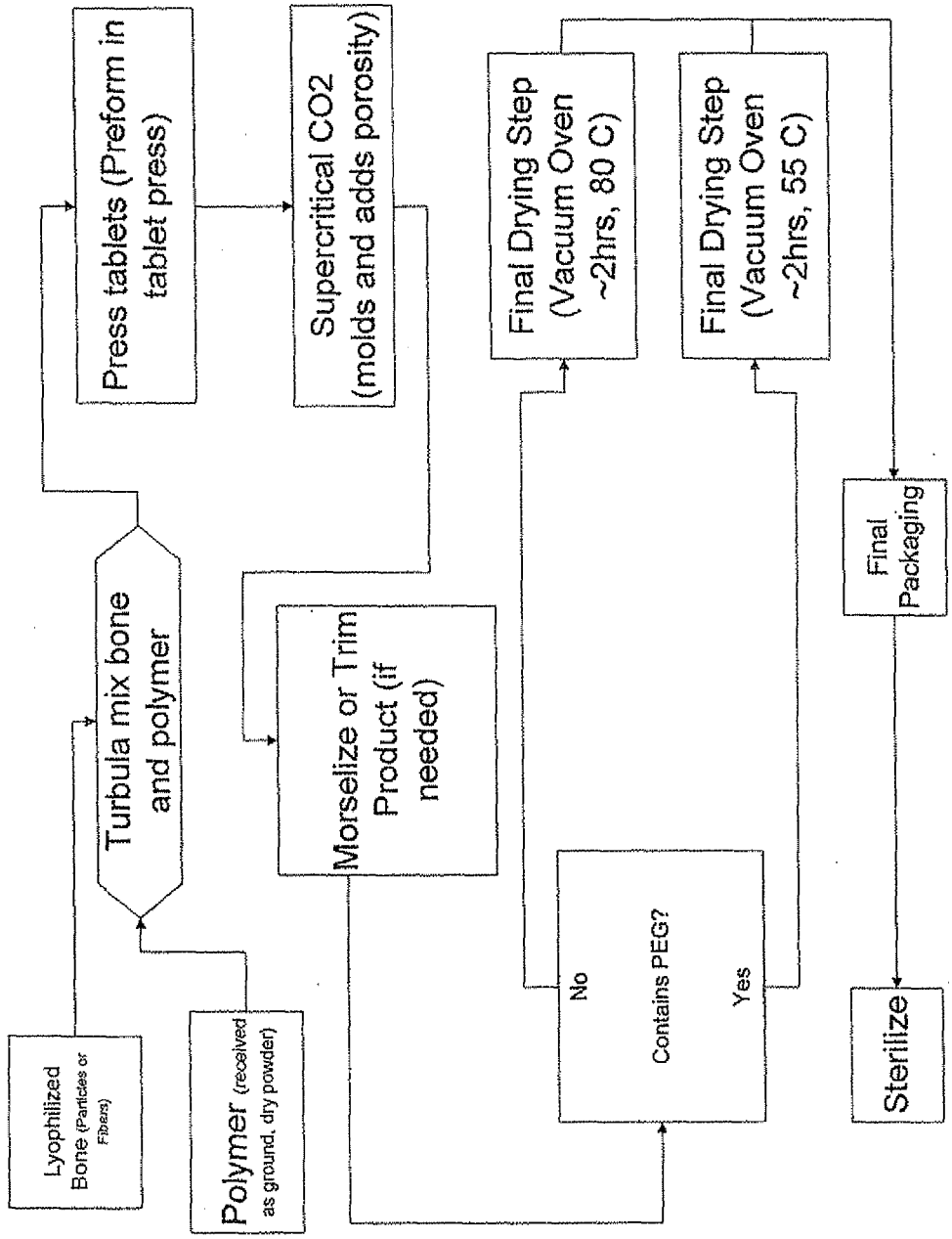
FIG. 1 presents a process diagram for an exemplary method of producing porous composites according to an embodiment of the present invention.

Throughout the specification, several terms are employed that are defined in the following paragraphs.

As used herein, "bioactive agent" is used to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, mitotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain preferred embodiments, the bioactive agent is a drug. In certain embodiments, the bioactive agent is a small molecule.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "*Merck Index: An Encyclopedia of Chemicals, Drugs, and Biologicals*", Edited by Susan Budavari et al., CRC Press, 1996, the United States Pharmacopeia-25/National Formulary-20, published by the United States Pharmcopeial Convention, Inc., Rockville Md., 2001, and the "*Pharmazeutische Wirkstoffe*", edited by Von Keemann et al., Stuttgart/New York, 1987, all of which are incorporated herein by reference. Drugs for human use listed by the U.S. Food and Drug Administration (FDA) under 21 C.F.R. §§330.5, 331 through 361, and 440 through 460, and drugs for veterinary use listed by the FDA under 21 C.F.R. §§500 through 589, all of which are incorporated herein by reference, are also considered acceptable for use in accordance with the present invention.

As used herein, the term "biocompatible" is intended to describe any material which upon implantation does not elicit a substantial detrimental response in vivo.

The terms "biodegradable", "bioerodable" and "resorbable" are used herein interchangeably. When used to characterize materials, they refer to materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Other degradation mechanisms, e.g., thermal degradation due to body heat, are also envisioned. Biodegradable materials also include materials that are broken down within cells. Degradation may occur by hydrolysis, enzymatic processes, phagocytosis, or other processes.

The term "biomolecules", as used herein, refers to the class of molecules (e.g., proteins, amino acids, peptides, polynucleotides, nucleotides, carbohydrates, sugars, lipids, glycoproteins, nucleoproteins, lipoproteins, steroids, etc) that are commonly found in cells or tissues, whether the molecules themselves are naturally-occurring or artificially created (e.g., by synthetic or recombinant methods). For example, biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

As used herein, the term "composite" refers to a unified combination of two or more distinct materials. The composite may be homogeneous or heterogeneous. For example, a composite may be a composition of bone-derived particles and a polymer; or a combination of bone substitute material and a polymer. In certain embodiments, the composite has a particular orientation.

The term "demineralized", when used herein to characterize bone particles, refers to bone particles that have been subjected to a process that caused a decrease in their original inorganic content. As used herein, the term "superficially demineralized" as applied to the bone particles refers to bone particles possessing at least about 90 weight percent of their original inorganic mineral content. The term "partially demineralized" as applied to the bone particles refers to bone particles possessing from about 8 to about 90 weight percent of their original inorganic mineral content, and the term "fully demineralized" as applied to the bone particles refers to bone particles possessing less than about 8, preferably less than about 1, weight percent of their original inorganic mineral content. The unmodified term "demineralized" as applied to the bone particles is intended to cover any one or combination of the foregoing types of demineralized bone particles.

The terms "load bearing" and "weight bearing" are used herein interchangeably. They refer to a bone product for implantation in a patient at a site where the bone graft is expected to withstand some level of physical load or force.

The term "mechanical strength", as used herein, refers to those properties exhibited by a bone graft or bone product including loading strength, compressive strength, and tensile strength.

The terms "mineralized" and "deorganified" are used herein interchangeably, and refer to bone or cartilage matrices, particles, etc. that have been subjected to a process that caused a decrease in their original organic content (e.g., degreasing or de-fatting). Such a process results in an increase in an increase in the relative inorganic mineral content of the bone or cartilage matrices, particles, etc. In some embodiments, at least 1%, 10%, 20%, 30%, 40%, 50%, 60%, 70%, 80%, 90% or 99% of the organic content of the starting material is removed. Deorganified bone from which substantially all the organic components have been removed is termed "anorganic".

The term "non-demineralized", when used herein to characterize bone particles, refers to bone particles that have not been subjected to a demineralization process (i.e., a procedure that caused a decrease in the original inorganic content of the bone particles).

The term "osteoconductive", as used herein, refers to the ability of a substance or material to provide biologically inert surfaces which are receptive to the growth of new host bone.

The term "osteogenic", as used herein, refers to the ability of a substance or material to induce new bone formation via the participation of living cells from within the substance.

The term "osteoimplant" is used herein in its broadest sense and is not intended to be limited to any particular shapes, sizes, configurations or applications. It refers to any device or material for implantation that aids or augments bone formation or healing. Osteoimplants are often applied at a bone defect site, e.g., one resulting from injury, defect brought about during the course of surgery, infection, malignancy or developmental malformation. Osteoimplants can be used in a variety of orthopedic, neurosurgical, and oral and maxillofacial surgical procedures such as the repair of simple and compound fractures and non-unions, external and internal fixations, joint reconstructions such as arthrodesies, general arthroplasty, deficit filling, discectomy, laminectomy, anterior cervical and thoracic operations, spinal fusions, etc. They may also be used to attach non-bony tissues to bone, such as tendon, cartilage, synovium, etc.

The term "osteoinductive", as used herein, refers to the ability of a substance or material to recruit cells from the host, that have the potential for repairing the bone tissue.

The term "plasticizer", as used herein, refers to an additive that softens hard polymers or plastics. The plasticizer makes the polymer formable or flexible. Plasticizers are thought to work by embedding themselves between the chains of polymers, spacing them apart, and thus lowering the glass transition temperature. Preferably, the plasticizers used in the inventive composites are non-toxic and biocompatible. In certain embodiments, as the plasticizer diffuses out of the composite osteoimplant the composite loses its formability.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as RNAi, siRNA, or shRNA.

As used herein, a "polypeptide", "peptide", or "protein" includes a string of at least three amino acids linked together by peptide bonds. The terms "polypeptide", "peptide", and "protein", may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide", as used herein, refer to any polymer or oligomer of carbohydrate residues. The polymer or oligomer may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.)

and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen" refers to a chemical compound that can be part of the inventive composite and upon implantation or prior to implantation diffuses, dissolves, and/or degrades to leave a pore in the osteoimplant composite. The porogen essentially reserves space in the composite while the composite is being molded but once the composite is implanted the porogen diffuses, dissolves, or degrades, thereby inducing porosity into the composite. In this way the porogen provides "latent pores". The porogen may also be leached out of the composite before implantation. This resulting porosity of the implant is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars, polysaccharides, water soluble small molecules, etc. Porogen can also be natural or synthetic polymers that are water soluble or degrade quickly under physiological conditions. Exemplary polymers include poly(vinylpyrollidone), pullulan, poly(glycolide), poly(lactide), poly(lactide-co-glycolide), other polyesters, and starches.

The terms "porosity" and "void volume" are used herein interchangeably and refer to the average amount of non-solid space contained in a material (e.g., a composite of the present invention). Such space is considered void of volume even if it contains a substance that is liquid at ambient or physiological temperature, e.g., 0.5° C. to 50° C. The porosity or void volume of a composite can be defined as the ratio of the total volume of the pores (i.e., void volume) in the material to the overall volume of the composite.

The term "shaped", as used herein to characterize a material (e.g., composite) or an osteoimplant, refers to a material or osteoimplant of a determined or regular form or configuration in contrast to an indeterminate form or vague form or configuration (as in the case of a lump or other solid matrix of special form). Materials can be shaped as sheets, blocks, plates, disks, cones, pins, screws, tubes, teeth, bones, portion of bones, wedges, cylinders, threaded cylinders, and the like, as well as more complex configurations, and anatomic shapes.

The term "small molecule", as used herein, refers to molecules, whether naturally-occurring or artificially created (e.g., via chemical synthesis) that have a relatively low molecular weight. Typically, small molecules are monomeric and have a molecular weight of less than about 1500 Da. In the context of the present invention, preferred small molecules are biologically active in that they produce a local or systemic effect in the patient. In certain embodiments, the small molecule is a drug. Preferably, though not necessarily, the drug is one that has already been deemed safe and effective for use by an appropriate governmental agency or body.

As used herein, the term "supercritical fluid" has its art understood meaning and refers to a substance at a temperature and pressure above its thermodynamic critical point. Under these conditions, the distinction between gases and liquids does not apply and the substance can only be described as a fluid. Under these conditions, a supercritical fluid has the unique ability to diffuse through solids like a gas, and dissolve materials like a liquid. Additionally, a supercritical fluid can readily change in density upon minor changes in temperature or pressure.

As used herein, the term "supercritical carbon dioxide or $SCCO_2$," has its art understood meaning and refers to $CO_2$ above its thermodynamic critical point (i.e., above critical temperature of 31.1° C. and pressure of 73 atm). $SCCO_2$ is an excellent non-polar solvent for many organic compounds. It has been likened to a solvent resembling hexane, though with some hydrogen-bonding acceptor capability and some dipole selectivity. Alkenes, alkanes, aromatics, ketones, and alcohols (up to a relative molecular mass of around 400) dissolve in $SCCO_2$. Very polar molecules such as sugars or amino acids and most inorganic salts are insoluble. By adjusting the pressure of the fluid, the solvent properties can be adjusted to more "gas-like" or more "liquid-like", which allows tuning of the solvent properties.

As used herein, the term "targeting agent" refers to any chemical entity which, when included in a composite, will direct the composite to a particular site or cause the composite to remain in a particular site within the recipient's body. A targeting agent may be a small molecule, peptide, protein, polynucleotide, etc. Typical targeting agents are antibodies, ligands of known receptors, and receptors.

The term "tissue-derived material", as used herein, refers to a material that is obtained from an mammal tissue. A tissue-derived material may include the tissue itself, a portion thereof, or one or more components thereof. For example, bone-derived tissue includes a whole bone, a bone particle, and bone or bone pieces that have been processed to remove one or more of cells, collagen, other extracellular matrix components, mineral, etc. In certain embodiments, tissue-derived material is treated to removed any infectious agents, in particular, pathogens (e.g., viruses, bacteria, fungi, parasites, etc.) In certain embodiments, tissue-derived material is treated to kill or remove any living cells or viruses. In certain particular embodiments, the tissue-derived material includes the extracellular matrix portion of a tissue. In certain embodiments, the tissue-derived material is purified extracellular matrix.

As used herein, the term "transformation" describes the process by which a material is removed from an implant site and replaced by host tissue after implantation. Transformation may be accomplished by a combination of processes, including but not limited to remodeling, degradation, resorption, and tissue growth and/or formation. Removal of the material may be cell-mediated or accomplished through chemical processes, such as dissolution and hydrolysis.

DETAILED DESCRIPTION OF CERTAIN PREFERRED EMBODIMENTS

As mentioned above, the present invention provides porous composites for bone repair. The inventive composites comprise a polymer and a plurality of particles of inorganic material, bone-derived material, bone substitute material, and/or composite material. The inventive porous composites may be prepared using any of a variety of methods. In certain embodiments, the inventive composites are prepared using a method that includes a supercritical fluid (e.g., supercritical carbon dioxide) treatment. The composites can be used in a large variety of clinical applications, for example as bone void fillers, to repair or help healing of skeletal deficiencies resulting from trauma, tumors, surgery, iatrogenic, congenital, genetic, metabolic and degenerative or abnormal development, and inflammatory infection. Upon implantation, the inventive composites promote cellular infiltration from adjacent osseous tissues, thus accelerating the remodeling process.

Certain aspects of preferred embodiments of the invention are described below in more detail. Those of ordinary skill will appreciate that a variety of embodiments or versions of the invention are not specifically discussed but are nonetheless within the scope of the present invention, as defined by the appended claims.

I—Inventive Composites and Preparation Thereof

A—Particles

Particles suitable for use in the present invention may include a bone-derived material, an inorganic material, a bone substitute material, a composite material, or any combinations thereof.

Bone-derived Particles

Any type of particles comprising inorganic material, bone substitute material, bone-derived material, or combinations or composites thereof may be utilized in the present invention. The bone or bone-derived particles employed in the composites of the present invention can be obtained from cortical, cancellous, and/or cortico-cancellous bone which may be of autogenous, allogenic, and/or xenogenic origin. The bone-derived material may be derived from any vertebrate. In certain embodiments, it is preferred that the source of the bone be matched to the eventual recipient of the inventive composition (i.e., the donor and recipient should, at least, be of the same species). For example, human bone-derived material is typically used in a human subject. In other embodiments, the bone particles are obtained from bone of xenogenic origin. Porcine bone and bovine bone are particularly advantageous types of xenogenic bone tissue that can be used individually or in combination as sources for the bone particles. Xenogenic bone tissue may be combined with allogenic or autogenous bone.

Preparation of Bone Particles. Methods for the Preparation of Bone Particles are known in the art. Bone particles can be formed by milling whole bone to produce fibers, chipping whole bone, cutting whole bone, fracturing whole bone in liquid nitrogen, or otherwise disintegrating the bone tissue. In certain embodiments, particles are sieved to produce particles of a specific size range. Bone particles may be of any shape or size. Exemplary shapes include spheroidal, plates, fibers, cuboidal, sheets, rods, oval, strings, elongated particles, wedges, discs, rectangular, polyhedral, etc. In some embodiments, bone particles may be between about 10 microns and about 1000 microns in diameter or more. In some embodiments, particles may be between about 20 microns and about 800 microns in diameter or more. In certain embodiments, the particles range in size from approximately 100 microns in diameter to approximately 500 microns in diameter. In certain embodiments, the particles range in size from approximately 300 microns in diameter to approximately 800 microns in diameter. As for irregularly shaped particles, the recited dimension ranges may represent the length of the greatest or smallest dimension of the particle.

In certain embodiments, the particle size distribution of the particles that are combined with a polymer to form the inventive composite with respect to a mean value may be plus or minus, e.g., about 10% or less of the mean value, about 20% or less of the mean value, about 30% or less of the mean value, about 40% or less of the mean value, about 50% or less of the mean value, about 60% or less of the mean value, about 70% or less of the mean value, about 80% or less of the mean value, or about 90% or less of the mean value. In other embodiments, the particle size distribution of the particles that are combined with a polymer to form the inventive composite with respect to a median value may be plus or minus, e.g., about 10% or less of the median value, about 20% or less of the median value, about 30% or less of the median value, about 40% or less of the median value, about 50% or less of the median value, about 60% or less of the median value, about 70% or less of the median value, about 80% or less of the median value, or about 90% or less of the median value. In certain embodiments, at least about 60, 70, or 80 weight percent of the particles posses a median length of about 10 microns to about 1000 microns in their greatest dimension. In certain embodiments, at least about 60, 70, or 80 weight percent of the particles posses a median length of about 20 microns to about 800 microns in their greatest dimension. For particles that are fibers or other elongated particles, at least about 80 weight percent, at least about 70 weight percent, or at least about 60 weight percent of the particles possess a median length of from about 2 to about 200 mm, or more preferably from about 10 to about 100 mm, a median thickness of from about 0.05 to about 2 mm, and preferably from about 0.2 to about 1 mm, and a median width of from about 1 mm to about 20 mm and preferably from about 2 to about 5 mm. The particles may possess a median length to median thickness ratio of at least about 50:1 up to about 500:1 or more and preferably from about 50:1 up to about 100:1 and a median length to median width ratio of from about 10:1 to about 200:1 and preferably from about 50:1 to about 100:1. In certain embodiments, the bone-derived particles are short fibers having a cross-section of about 300 microns to about 800 microns and a length of about 1 mm to about 5 mm.

The composite of the invention can be made using bone-derived particles of a single shape or of different shapes. In the latter case, the mechanical properties of the final composite can be tailored by adjusting the weight percent of the various shapes of bone particles.

Modification of the Components of Bone Particles. In certain embodiments, the bone-derived particles are used "as is" in preparing the inventive composites. In other embodiments, the bone-derived particles are modified before composite preparation. Thus, for example, bone particles suitable for use in the methods of the present invention can be demineralized, non-demineralized, mineralized/deorganified, or anorganic bone particles.

For example, bone particles can be demineralized in accordance with known and conventional procedures in order to reduce their inorganic mineral content. Demineralization methods remove the inorganic mineral component of bone by employing acid solutions. Such methods are well known in the art (see, for example, Reddi et al., Proc. Natl. Acad. Sci., 1972, 69: 1601-1605). The strength of the acid solution, the shape of the bone particles and the duration of the demineralization treatment will determine the extent of demineralization (Lewandrowski et al., J. Biomed. Mater. Res., 1996, 31: 365-372 and U.S. Pat. No. 5,290,055, incorporated herein by reference).

In certain embodiments, bone particles are subjected to a process that partially or totally removes their initial organic content to yield mineralized and anorganic bone particles, respectively. Different mineralization methods have been developed and are known in the art (Hurley et al., Milit. Med., 1957, 101-104; Kershaw, Pharm. J., 1963, 8: 537; and U.S. Pat. No. 4,882,149, each of which is incorporated herein by reference). For example, a mineralization procedure can include a de-greasing step followed by a basic treatment (with ammonia or an amine) to degrade residual proteins and an extensive water washing (U.S. Pat. Nos. 5,417,975 and 5,573,771, each of which is incorporated herein by reference). Another example of mineralization procedure include a defatting step where bone particles are sonicated in 70% ethanol for between 1 and 3 hours.

Another example of preparation method includes a defatting/disinfecting step, followed by an acid demineralization step. As already mentioned above, the solution used in the defatting/disinfecting step can be an aqueous solution of an alcohol (e.g., about 60 to about 90 weight percent of ethanol), which produces optimal lipid removal and disinfection within the shortest period of time. Following defatting, the bone particles are immersed in acid over time to effect their demineralization. The acid also disinfects the bone by killing viruses, vegetative microorganisms, and spores. Acids which can be employed in this step include inorganic acids such as hydrochloric acid and organic acids such as peracetic acid. After acid treatment, the demineralized bone particles are rinsed with sterile water to remove residual amounts of acid and thereby raise the pH. The bone particles may be dried, for example, by lyophilization, before combination with the polymer. The bone particles may be stored under aseptic conditions, for example, in a lyophilized state, until they are used, or sterilized using known methods shortly before combining them with the polymer.

Other organic solvent may also be used in the defatting and disinfecting the particles. For example, methanol, isopropanol, butanol, DMF, DMSO, diethyl ether, hexanes, glyme, tetrahydrofuran, chloroform, methylene chloride, and carbon tetrachloride may be used. In certain embodiments, a nonhalogenated solvent is used. The defatting/disinfectant solution may also include a detergent (e.g., an aqueous solution of a detergent). Ordinarily, at least about 10 to about 40 percent by weight of water (i.e., about 60 to about 90 weight percent of defatting agent such as alcohol) should be present in the defatting/disinfecting solution to produce optimal lipid removal and disinfection within the shortest period of time.

In an exemplary defatting/disinfecting/demineralization procedure, the bone particles are subjected to a defatting/disinfecting step, followed by an acid demineralization step. An exemplary defatting/disinfectant solution is an aqueous solution of ethanol. Ordinarily, at least about 10 to about 40 percent by weight of water (i.e., about 60 to about 90 weight percent of defatting agent such as alcohol) should be present in the defatting/disinfecting solution to produce optimal lipid removal and disinfection within a reasonable period of time. An exemplary concentration range of the defatting solution is from about 60 to about 85 weight percent alcohol, for example, about 70 weight percent alcohol. Ethanol is typically the alcohol used in this step; however, other alcohols such as methanol, propanol, isopropanol, denatured ethanol, etc. may also be used. Following defatting, the bone particles are immersed in acid over time to effect their demineralization. The acid also disinfects the bone by killing viruses, vegetative microorganisms, and spores. Acids which can be employed in this step include inorganic acids such as hydrochloric acid and organic acids such as peracetic acid. After acid treatment, the demineralized bone particles are rinsed with sterile water to remove residual amounts of acid and thereby raise the pH. The bone particles may be dried, for example, by lyophilization, before being incorporated into the composite. The bone particles may be stored under aseptic conditions, for example, in a lyophilized state, until they are used or sterilized using known methods (e.g., gamma irradiation) shortly before combining them with a polymer.

As utilized herein, the phrase "superficially demineralized" as applied to the bone particles refers to bone particles possessing at least about 90% by weight of their original inorganic mineral content. The phrase "partially demineralized" as applied to the bone particles refers to bone particles possessing from about 8% to about 90% weight of their original inorganic mineral content, and the phrase "fully demineralized" as applied to the bone particles refers to bone particles possessing less than about 8%, preferably less than about 1%, by weight of their original inorganic mineral content. The unmodified term "demineralized" as applied to the bone particles is intended to cover any one or combination of the foregoing types of demineralized bone particles, that is, superficially demineralized, partially demineralized, or fully demineralized bone particles.

In an alternative embodiment, surfaces of bone particles may be lightly demineralized according to the procedures in our commonly owned U.S. patent application, U.S. Ser. No. 10/285,715, filed Nov. 1, 2002, published as U.S. Patent Publication No. 2003/0144743, on Jul. 31, 2003, the contents of which are incorporated herein by reference. Even minimal demineralization, for example, of less than 5% removal of the inorganic phase, increases the hydroxylation of bone fibers and the surface concentration of amine groups. Demineralization may be so minimal, for example, less than 1%, that the removal of the calcium phosphate phase is almost undetectable. Rather, the enhanced surface concentration of reactive groups defines the extent of demineralization. This may be measured, for example, by titrating the reactive groups.

In one embodiment, in a polymerization reaction that utilizes the exposed allograft surfaces to initiate a reaction, the amount of unreacted monomer remaining may be used to estimate reactivity of the surfaces. Surface reactivity may be assessed by a surrogate mechanical test, such as a peel test of a treated coupon of bone adhering to a polymer.

In certain embodiments, the bone-derived particles are subjected to a process that partially or totally removes their initial organic content to yield mineralized and anorganic bone particles, respectively. Different mineralization methods have been developed and are known in the art (Hurley et al., *Milit. Med.* 1957, 101-104; Kershaw, *Pharm. J.* 6:537, 1963; and U.S. Pat. No. 4,882,149; each of which is incorporated herein by reference). For example, a mineralization procedure can include a de-greasing step followed by a basic treatment (with ammonia or another amine) to degrade residual proteins and a water washing (U.S. Pat. Nos. 5,417,975 and 5,573,771; both of which are incorporated herein by reference). Another example of a mineralization procedure includes a defatting step where bone particles are sonicated in 70% ethanol for 1-3 hours.

If desired, the bone-derived particles can be modified in one or more ways, e.g., their protein content can be augmented or modified as described, for example, in U.S. Pat. Nos. 4,743,259 and 4,902,296, the contents of both of which are incorporated herein by reference.

Mixtures or combinations of one or more of the foregoing types of bone-derived particles can be employed in the present invention. For example, one or more of the foregoing types of demineralized bone particles can be employed in combination with non-demineralized bone particles and or mineralized bone particles. The amount of each individual type of bone particles employed can vary depending on the mechanical and biological properties desired. Thus, mixtures of bone particles of various shapes, sizes, and/or degree of demineralization and/or mineralization may be assembled based on the desired mechanical, thermal, and biological properties of the composite. Suitable amounts of particle types can be readily determined by those skilled in the art on a case-by-case basis by routine experimentation.

Modification of the Components of Bone Particles. The bone-derived particles may be optionally treated to enhance their interaction with the polymer of the composite or to confer some property to the particle surface. While some bone-derived particles will interact readily with the monomer and be covalently linked to the polymer matrix, it may be desirable to modify the surface of the bone-derived particles to facilitate incorporation into polymers that do not bond well to bone, such as poly(lactides). Surface modification may provide a chemical substance that is strongly bonded to the surface of the bone, e.g., covalently bonded to the surface. The bone-derived particles may also be coated with a material to facilitate interaction with the polymer of the composite.

In one embodiment, silane coupling agents are employed to link a monomer or initiator molecule to the surface of the bone-derived particles. The silane has at least two sections, a set of three leaving groups and an active group. The active group may be connected to the silicon atom in the silane by an elongated tether group. An exemplary silane coupling agent is 3-trimethoxysilylpropylmethacrylate, available from Union Carbide. The three methoxy groups are the leaving groups, and the methacrylate active group is connected to the silicon atom by a propyl tether group. In one embodiment, the leaving group is an alkoxy group such as methoxy or ethoxy. Depending on the solvent used to link the coupling agent to the bone-derived particle, hydrogen or alkyl groups such as methyl or ethyl may serve as the leaving group. The length of the tether determines the intimacy of the connection between the polymer matrix and the bone-derived particle. By providing a spacer between the bone-derived particle and the active group, the tether also reduces competition between chemical groups at the particle surface and the active group and makes the active group more accessible to the monomer during polymerization.

In one embodiment, the active group is an analog of the monomer of the polymer used in the composite. For example, amine active groups will be incorporated into polyamides, polyesters, polyurethanes, polycarbonates, polycaprolactone, and other polymer classes based on monomers that react with amines, even if the polymer does not contain an amine. Hydroxy-terminated silanes will be incorporated into polyamino acids, polyesters, polycaprolactone, polycarbonates, polyurethanes, and other polymer classes that include hydroxylated monomers. Aromatic active groups or active groups with double bonds will be incorporated into vinyl polymers and other polymers that grow by radical polymerization (e.g., polyacrylates, polymethacrylates). It is not necessary that the active group be monofunctional. Indeed, it may be preferable that active groups that are to be incorporated into polymers via step polymerization be difunctional. A silane having two amines, even if one is a secondary amine, will not terminate a polymer chain but can react with ends of two different polymer chains. Alternatively, the active group may be branched to provide two reactive groups in the primary position.

An exemplary list of silanes that may be used with the invention is provided in U.S. Patent Publication No. 2004/0146543, the contents of which are incorporated herein by reference. Silanes are available from companies such as Union Carbide, AP Resources Co. (Seoul, South Korea), and BASF. Where the silane contains a potentially non-biocompatible moiety as the active group, it should be used to tether a biocompatible compound to the bone particle using a reaction in which the non-biocompatible moiety is the leaving group. It may be desirable to attach the biocompatible compound to the silane before attaching the silane to the bone-derived particle, regardless of whether the silane is biocompatible or not. The derivatized silanes may be mixed with silanes that can be incorporated directly into the polymer and reacted with the bone-derived particles, coating the bone particles with a mixture of "bioactive" silanes and "monomer" silanes. U.S. Pat. No. 6,399,693, the contents of which are incorporated herein by reference discloses composites of silane modified polyaromatic polymers and bone. Silane-derivatized polymers may be used in the inventive composites instead of or in addition to first silanizing the bone-derived particles.

The active group of the silane may be incorporated directly into the polymer or may be used to attach a second chemical group to the bone particle. For example, if a particular monomer polymerizes through a functional group that is not commercially available as a silane, the monomer may be attached to the active group.

Non-silane linkers may also be employed to produce composites according to the invention. For example, isocyanates will form covalent bonds with hydroxyl groups on the surface of hydroxyapatite ceramics (de Wijn, et al., "Grafting PMMA on Hydroxyapatite Powder Particles using Isocyanatoethylmethacrylate," Fifth World Biomaterials Congress, May 29-Jun. 2, 1996, Toronto, Calif.). Isocyanate anchors, with tethers and active groups similar to those described with respect to silanes, may be used to attach monomer-analogs to the bone particles or to attach chemical groups that will link covalently or non-covalently with a polymer side group. Polyamines, organic compounds containing one or more primary, secondary, or tertiary amines, will also bind with both the bone particle surface and many monomer and polymer side groups. Polyamines and isocyanates may be obtained from Aldrich.

Alternatively, a biologically active compound such as a biomolecule, a small molecule, or a bioactive agent may be attached to the bone-derived particle through the linker. For example, mercaptosilanes will react with the sulfur atoms in proteins to attach them to the bone-derived particle. Aminated, hydroxylated, and carboxylated silanes will react with a wide variety functional groups. Of course, the linker may be optimized for the compound being attached to the bone-derived particle.

Biologically active molecules can modify non-mechanical properties of the composite as it is degraded. For example, immobilization of a drug on the bone particle allows it to be gradually released at an implant site as the composite is degraded. Anti-inflammatory agents embedded within the composite will control the inflammatory response long after the initial response to injection of the composite. For example, if a piece of the composite fractures several weeks after injection, immobilized compounds will reduce the intensity of any inflammatory response, and the composite will continue to degrade through hydrolytic or physiological processes. Compounds may also be immobilized on the bone-derived particles that are designed to elicit a particular metabolic response or to attract cells to the injection site.

Some biomolecules, small molecules, and bioactive agents may also be incorporated into the polymer used in the composite. For example, many amino acids have reactive side chains. The phenol group on tyrosine has been exploited to form polycarbonates, polyarylates, and polyiminocarbonates (see Pulapura, et al., "Tyrosine-derived polycarbonates: Backbone-modified "pseudo"-poly(amino acids) designed for biomedical applications," *Biopolymers*, 1992, 32: 411-417; and Hooper, et al., "Diphenolic monomers derived from the natural amino acid α-L-tyrosine: an evaluation of peptide coupling techniques," *J. Bioactive and Compatible Polymers*, 1995, 10:327-340, the entire contents of both of which are incorporated herein by reference). Amino acids such as lysine, arginine, hydroxylysine, proline, and hydroxyproline also have reactive groups and are essentially tri-functional. Amino acids such as valine, which has an isopropyl side chain, are still difunctional. Such amino acids may be attached to the silane and still leave one or two active groups available for incorporation into a polymer.

Non-biologically active materials may also be attached to the bone particles. For example, radiopaque, luminescent, or magnetically active particles may be attached to the bone particles using the techniques described above. If a material, for example, a metal atom or cluster, cannot be produced as a silane or other group that reacts with calcium phosphate ceramics, then a chelating agent may be immobilized on the bone particle surface and allowed to form a chelate with the atom or cluster. As the bone is resorbed, these non-biodegradable materials are still removed from the tissue site by natural metabolic processes, allowing the degradation of the polymer and the resorption of the bone-derived particles to be tracked using standard medical diagnostic techniques.

In an alternative embodiment, the bone-derived particle surface is chemically treated before being derivatized or combined with a polymer. For example, non-demineralized bone-derived particles may be rinsed with phosphoric acid, e.g., for 1 to 15 minutes in a 5-50% solution by volume. Those skilled in the art will recognize that the relative volume of bone particles and phosphoric acid solution (or any other solution used to treat the bone particles), may be optimized depending on the desired level of surface treatment. Agitation will also increase the uniformity of the treatment both along individual particles and across an entire sample of particles. The phosphoric acid solution reacts with the mineral component of the bone to coat the particles with calcium phosphate, which may increase the affinity of the surface for inorganic coupling agents such as silanes and for the polymer component of the composite. As noted above, the surface may be partially demineralized to expose the collagen fibers at the particle surface.

The collagen fibers exposed by demineralization are typically relatively inert but have some exposed amino acid residues that can participate in reactions. The collagen may be rendered more reactive by fraying the triple helical structure of the collagen to increase the exposed surface area and the number of exposed amino acid residues. This not only increases the surface area available for chemical reactions but also for mechanical interaction with the polymer as well. Rinsing the partially demineralized bone particles in an alkaline solution will fray the collagen fibrils. For example, bone particles may be suspended in water at a pH of about 10 for about 8 hours, after which the solution is neutralized. One skilled in the art will recognize that this time period may be increased or decreased to adjust the extent of fraying. Agitation, for example, in an ultrasonic bath, may reduce the processing time. Alternatively, the particles may be sonicated with water, surfactant, alcohol, or some combination of these.

Alternatively, the collagen fibers may be cross-linked. A variety of cross-linking techniques suitable for medical applications are well known in the art (see, for example, U.S. Pat. No. 6,123,781, the contents of which are incorporated herein by reference). For example, compounds like 1-ethyl-3-(3-dimethylaminopropyl) carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, "Evaluation of collagen cross-linking techniques for the stabilization of tissue matrices," *Biotechnol. Appl. Biochem.*, 1993, 17:23-29; PCT Publication WO98/19718, the contents of both of which are incorporated herein by reference). Alternatively, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link the collagen. The bone-derived particles are then washed to remove all leachable traces of the material. Enzymatic cross-linking agents may also be used. Additional cross-linking methods include chemical reaction, irradiation, application of heat, dehydrothermal treatment, enzymatic treatment, etc. One skilled in the art will easily be able to determine the optimal concentrations of cross-linking agents and incubation times for the desired degree of cross-linking.

Both frayed and unfrayed collagen fibers may be derivatized with monomer, pre-polymer, oligomer, polymer, initiator, and/or biologically active or inactive compounds, including but not limited to biomolecules, bioactive agents, small molecules, inorganic materials, minerals, through reactive amino acids on the collagen fiber such as lysine, arginine, hydroxylysine, proline, and hydroxyproline. Monomers that link via step polymerization may react with these amino acids via the same reactions through which they polymerize. Vinyl monomers and other monomers that polymerize by chain polymerization may react with these amino acids via their reactive pendant groups, leaving the vinyl group free to polymerize. Alternatively, or in addition, bone-derived particles may be treated to induce calcium phosphate deposition and crystal formation on exposed collagen fibers. Calcium ion association to the surface provides a biocompatible surface, which allows for the attachment of cells as well as crystal growth. The polymer will interact with these fibers, increasing interfacial area and improving the wet strength of the composite.

Additionally or alternatively, the surface treatments described above or treatments such as etching may be used to increase the surface area or surface roughness of the bone-derived particles. Such treatments increase the interfacial strength of the particle/polymer interface by increasing the surface area of the interface and/or the mechanical interlocking of the bone-derived particles and the polymer. Such surface treatments may also be employed to round the shape or smooth the edges of bone particles to facilitate delivery of the inventive composite. Such treatment is particularly useful for injectable composites.

In some embodiments, surface treatments of the bone-derived particles are optimized to enhance covalent attractions between the bone-derived particles and the polymer of the composite. In an alternative embodiment, the surface treatment may be designed to enhance non-covalent interactions between the bone-derived particle and the polymer matrix. Exemplary non-covalent interactions include electrostatic interactions, hydrogen bonding, pi-bond interactions, hydrophobic interactions, van der Waals interactions, and mechanical interlocking. For example, if a protein or a polysaccharide is immobilized on the bone-derived particle, the chains of the polymer will become physically entangled with the long chains of the biological polymer when they are combined. Charged phosphate sites on the surface of the particles, produced by washing the bone particles in basic solution, will interact with the amino groups present in many biocompatible polymers, especially those based on amino acids. The pi-orbitals on aromatic groups immobilized on a bone-derived particle will interact with double bonds and aromatic groups of the polymer.

Additional Particulate Materials

In certain embodiments, the particles for use in the composite of the present invention are made of inorganic materials, including calcium phosphate materials and bone substitute materials. Exemplary inorganic materials suitable for use in the present invention include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, $\alpha$-tricalcium phosphate, dicalcium phosphate, $\beta$-tricalcium phosphate, tetracalcium phosphate, amorphous calcium phosphate, octacalcium phosphate, and BIOGLASS™, a calcium phosphate silica glass available from USBiomaterials Corporation (Jacksonville Beach, Fla.). Substituted calcium phosphate phases are also contemplated for use with the invention, including but not limited to fluorapatite, chlorapatite, Mg-substituted tricalcium phosphate, and carbonate hydroxyapatite. For example, the hydroxyapatite may be substituted with other ions such as fluoride, chloride, magnesium, sodium, potassium, etc. Additional calcium phosphate phases suitable for use with the invention include, for example, those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, *On Biomineralization*, Oxford University Press, 1989, each of which is incorporated herein by reference.

Composite Materials

In certain embodiments, a composite material is employed in the preparation of the composites of the present invention. For example, inorganic materials such as those described above or bone-derived materials may be combined with proteins such as BSA, collagen, or other extracellular matrix components to form a composite. Alternatively or additionally, inorganic materials or bone-derived materials may be combined with synthetic or naturally-derived polymers to for a composite using, for example, the techniques described in Applicant's co-pending applications: U.S. application Ser. No. 10/735,135 filed on Dec. 12, 2003, entitled "Formable and settable polymer bone composite and method of production thereof" and published under No. 2005-0008672; U.S. application Ser. No. 10/681,651 filed on Oct. 8, 2003, entitled "Coupling agents for orthopedic biomaterials" and published under No. 2005-0008620; and U.S. application Ser. No. 10/639,912, filed on Aug. 12, 2003, entitled "Synthesis of a bone-polymer composite material" and published under No. 2004-0146543, the contents of all of which are incorporated herein by reference. These composites may be lightly demineralized to expose the organic material at the surface of the composite before they are combined with a polymer.

In certain embodiments, the composite material is one described in Applicant's co-pending applications: U.S. patent Ser. No. 10/771,736 filed on Feb. 2, 2004 and published under No. 2005-0027033 and U.S. patent Ser. No. 11/336,127 filed on Jan. 19, 2006 and published under No. 2006-0216323, both of which are entitled "Polyurethanes for Osteoimplants". The contents of both applications are incorporated herein by reference. Composite materials described in these applications comprise a polyurethane matrix and a reinforcement embedded in the matrix. The polyurethane matrix may be formed by reaction of a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates) with an optionally hydroxylated biomolecule (e.g., a phospholipids, fatty acid, cholesterol, polysaccharide, starch, or a combination or modified form of any of the above) to form a biodegradable polymer, while the reinforcement comprises bone or a bone substitute (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these).

Particulate materials may be modified to increase the concentration of nucleophilic groups (e.g., amino and/or hydroxyl groups) at their surfaces using, for example, techniques described herein. In certain embodiments, the particles make up between about 10% and about 30% by weight of the composite. In certain embodiments, the particles make up between about 30% and about 50% by weight of the composite. In certain embodiments, the particles make up between about 40% and about 50% by weight of the composite. In certain embodiments, the particles make up between about 60% and about 75% by weight of the composite. In certain embodiments, the particles make up between about 45% and about 70% by weight of the composite. In certain embodiments, the particles make up between about 50% and about 65% by weight of the composite. In certain particular embodiments, the particles make up approximately 20%, 25%, 30%, or 40% by weight of the composite. In certain particular embodiments, the particles make up approximately 45%, 46%, 47%, 48%, 49%, 50%, 51%, 52%, 53%, 54%, 55%, 56%, 57%, 58%, 59%, 60%, 61%, 62%, 63%, 64%, or 65% by weight of the composite.

B—Polymers

Suitable polymers useful for the preparation of the inventive composites are preferably biocompatible polymers, that can be of natural or synthetic origin or a combination of natural and synthetic polymers. Biodegradable polymers may be preferable in some embodiments. Co-polymers and/or polymer blends may also be exploited. A variety of polymers suitable for use in the present invention are known in the art, many of which are listed in commonly owned applications: U.S. application Ser. No. 10/735,135 filed on Dec. 12, 2003, entitled "Formable and settable polymer bone composite and method of production thereof" and published under No. 2005-0008672; U.S. application Ser. No. 10/681,651 filed on Oct. 8, 2003, entitled "Coupling agents for orthopedic biomaterials" and published under No. 2005-0008620; and U.S. Provisional Appln. No. 60/760,538, filed on Jan. 19, 2006 and entitled "Injectable and Settable Bone Substitute Material", all of which are incorporated herein by reference.

A number of biodegradable and non-biodegradable biocompatible polymers suitable for use in the practice of the present invention are known in the field of polymeric biomaterials, controlled drug release and tissue engineering (see, for example, U.S. Pat. Nos. 6,123,727; 5,804,178; 5,770,417; 5,736,372; and 5,716,404 to Vacanti; U.S. Pat. Nos. 6,095, 148; and 5,837,752 to Shastri; U.S. Pat. No. 5,902,599 to Anseth; U.S. Pat. Nos. 5,696,175; 5,514,378; and 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; and 4,638,045 to Kohn; U.S. Pat. Appln. No. 2005-0013793 to Beckman; see also Langer, Acc. Chem. Res. 2000, 33: 94-101; Langer, J. Control Release, 1999, 62: 7-11; and Uhrich et al., Chem. Rev., 1999, 99: 3181-3198, the contents of all of which are incorporated herein by reference).

In certain embodiments, the polymer is biodegradable. Exemplary biodegradable materials include lactide-glycolide copolymers of any ratio (e.g., 85:15, 40:60, 30:70, 25:75, or 20:80), poly(L-lactide-co-D,L-lactide), polyglyconate, poly (arylates), poly(anhydrides), poly(hydroxy acids), polyesters, poly(ortho esters), poly(alkylene oxides), polycarbonates, poly(propylene fumarates), poly(propylene glycol-co fumaric acid), poly(caprolactones), polyamides, polyamino acids, polyacetals, polylactides, polyglycolides, poly(dioxanones), polyhydroxybutyrate, polyhydroxyvalyrate, polyhydroxybutyrate/valerate copolymers, poly(vinyl pyrrolidone), biodegradable polycyanoacrylates, biodegradable polyurethanes including glucose-based polyurethanes and lysine-based polyurethanes, and polysaccharides (e.g., chitin, starches, celluloses). Natural polymers, including collagen, polysaccharides, agarose, glycosaminoglycans, alginate, chitin, and chitosan, may also be employed. Tyrosine-based polymers, including but not limited to polyarylates and polycarbonates, may also be employed (see Pulapura, et al., Biopolymers, 1992, 32: 411-417; Hooper, et al., J. Bioactive and Compatible Polymers, 1995, 10:327-340, the contents of both of which are incorporated herein by reference). Monomers for tyrosine-based polymers may be prepared by reacting an L-tyrosine-derived diphenol compound with phosgene or a diacid (Hooper, 1995; Pulapura, 1992). Similar techniques may be used to prepare amino acid-based monomers of other amino acids having reactive side chains, including imines, amines, thiols, etc. The polymers described in U.S. patent Ser. No. 11/336,127 filed on Jan. 19, 2006 and published under No. 2006-0216323, which is entitled "Polyurethanes for Osteoimplants", may also be used in embodiments of the present invention. In one embodiment, the degradation products include bioactive materials, biomolecules, small molecules, or other such materials that participate in metabolic processes.

Non-biodegradable polymers may also be used in the present invention. For example, polypyrrole, polyanilines, polythiophene, and derivatives thereof are useful electroactive polymers that can transmit voltage from endogenous bone to an implant. Other non-degradable, yet biocompatible polymers include polystyrene, polyesters, polyureas, poly (vinyl alcohol), polyamides, poly(tetrafluoroethylene), and expanded polytetrafluoroethylene (ePTFE), poly(ethylene vinyl acetate), polypropylene, polyacrylate, non-biodegradable polycyano-acrylates, non-biodegradable polyurethanes, mixtures and copolymers of poly(ethyl methacrylate) with tetrahydrofurfuryl methacrylate, polymethacrylate, poly(methyl methacrylate), polyethylene, including ultra high molecular weight polyethylene (UHMWPE), polypyrrole, polyanilines, polythiophene, poly(ethylene oxide), poly(ethylene oxide co-butylene terephthalate), poly ether-ether ketones (PEEK), and polyetherketoneketones (PEKK). Monomers that are used to produce any of these polymers are easily purchased from companies such as Polysciences, Sigma, and Scientific Polymer Products.

Examples of preferred polymers for use with the invention include but are not limited to starch-poly(caprolactone), poly (caprolactone), poly(lactide), poly(D,L-lactide), poly(lactide-co-glycolide), poly(D,L-lactide-co-glycolide), polycarbonates, polyurethane, tyrosine polycarbonate, tyrosine polyarylate, poly(orthoesters), polyphosphazenes, polypropylene fumarate, polyhydroxyvalerate, polyhydroxy butyrate, acrylates, methacrylates, and co-polymers, mixtures, enantiomers, and derivatives thereof. In certain particular embodiments, the polymer is starch-poly(caprolactone), poly(caprolactone), poly(lactide), poly(D,L-lactide), poly (lactide-co-glycolide), poly(D,L-lactide-co-glycolide), polyurethane, or a co-polymer, mixture, enantiomer, or derivative thereof. In certain embodiments, the polymer is poly(D,L-lactide). In certain other embodiments, the polymer is poly (D,L-lactide-co-glycolide). In certain embodiments, the polymer is poly(caprolactone). In certain embodiments, the polymer is a poly(urethane). In certain embodiments, the polymer is tyrosine polycarbonate. In certain embodiments, the polymer is tyrosine polyarylate.

In certain embodiments, the polymer used in the inventive composite is poly(lactide-co-glycolide). The ratio of lactide and glycolide units in the polymer may vary. Particularly useful ratios are approximately 45-80% lactide to approximately 44-20% glycolide. In certain embodiments, the ratio is approximately 50% lactide to approximately 50% glycolide. In other certain embodiments, the ratio is approximately 65% lactide to approximately 45% glycolide. In other certain embodiments, the ratio is approximately 60% lactide to approximately 40% glycolide. In other certain embodiments, the ratio is approximately 70% lactide to approximately 30% glycolide. In other certain embodiments, the ratio is approximately 75% lactide to approximately 25% glycolide. In certain embodiments, the ratio is approximately 80% lactide to approximately 20% glycolide. In certain of the above embodiments, lactide is D,L-lactide. In other embodiments, lactide is L-lactide. In certain particular embodiments, RESOMER® 824 (poly-L-lactide-co-glycolide) (Boehringer Ingelheim) is used as the polymer in the composite. In certain particular embodiments, RESOMER® 504 (poly-D,L-lactide-co-glycolide) (Boehringer Ingelheim) is used as the polymer in the composite. In certain particular embodiments, PURASORB PLG (75/25 poly-L-lactide-co-glycolide) (Purac Biochem) is used as the polymer in the composite. In certain particular embodiments, PURASORB PG (polyglycolide) (Purac Biochem) is used as the polymer in the composite. In certain embodiments, the polymer is PEGylated-poly(lactide-co-glycolide). In certain embodiments, the polymer is PEGylated-poly(lactide). In certain embodiments, the polymer is PEGylated-poly(glycolide). In other embodiments, the polymer is polyurethane. In other embodiments, the polymer is polycaprolactone. In certain embodiments, the polymer is a co polymer of poly(caprolactone) and poly(lactide). For polyesters such as poly(lactide) and poly(lactide-co-glycolide), the inherent viscosity of the polymer ranges from about 0.4 dL/g to about 5 dL/g. In certain embodiments, the inherent viscosity of the polymer ranges from about 0.6 dL/g to about 2 dL/g. In certain embodiments, the inherent viscosity of the polymer ranges from about 0.6 dL/g to about 3 dL/g. In certain embodiments, the inherent viscosity of the polymer ranges from about 1 dL/g to about 3 dL/g. In certain embodiments, the inherent viscosity of the polymer ranges from about 0.4 dL/g to about 1 dL/g. For poly(caprolactone), the inherent viscosity of the polymer ranges from about 0.5 dL/g to about 1.5 dL/g. In certain embodiments, the inherent viscosity of the poly(caprolactone) ranges from about 1.0 dL/g to about 1.5 dL/g. In certain embodiments, the inherent viscosity of the poly(caprolactone) ranges from about 1.0 dL/g to about 1.2 dL/g. In certain embodiments, the inherent viscosity of the poly(caprolactone) is about 1.08 dL/g.

Those skilled in the art will recognize that this an exemplary, not a comprehensive, list of polymers appropriate for in vivo applications. Co-polymers, mixtures, and adducts of the above polymers may also be used in the practice of the present invention.

Polymers may be manipulated to adjust their degradation rates. The degradation rates of polymers are well characterized in the literature (see, for example, *"Handbook of Biodegradable Polymers"*, Domb et al., Eds., Harwood Academic Publishers, 1997, the entire content of which is incorporated herein by reference). In addition, increasing the cross-link density of a polymer tends to decrease its degradation rate. The cross-link density of a polymer may be manipulated during polymerization by adding a cross-linking agent or promoter. After polymerization, cross-linking may be increased by exposure to UV light or other radiation. Mixture of polymers, for example lactide and glycolide polymers, may be employed to manipulate both degradation rate and mechanical properties.

The polymer may be ground and sieved to give a particle size range on the same scale as the particles or fibers, although it is not necessary to match the aspect ratio. In certain embodiments, the polymer is ground and then sieved to a size range of about 200 microns to about 500 microns.

Both the particles and the polymer may be dried using techniques known to those skilled in the art and may be stored in a dessicator if necessary. In some embodiments, the particles, the polymer, or the mixture of particles and polymer may be placed in a pouch made of gas permeable material, such as Tyvek® which is commercially available from DuPont, surrounded by dessicant and heated. Tyvek® is especially suitable because, during the supercritical carbon dioxide process, it lets supercritical $CO_2$ in under pressure and then lets the gas out during decompression, without exploding.

C—Combining the Polymer and Particles

The polymer and particles may be combined by any suitable method known in the art. In certain embodiments, the polymer and particles are combined in a complex motion tumbler, for example, a TURBULA® mixer. After blending, the mixture may optionally be tabletted using a pharmaceutical press. Alternatively or additionally, the mixture may be produced by other methods known to those skilled in the art, e.g., casting, sintering, isostatic pressing, etc. Any of these techniques may be used to form a mixture having a pre-determined shape, essentially a pre-form. In certain embodiments, however, after blending, the mixture is not subjected to any additional process before being transferred to the stainless cylindrical containers prior to the supercritical $CO_2$ treatment.

The ratio of particles to polymer in the mixture may be from about 80/20 to about 50/50, for example, about 70/30, about 69/31, about 68/32, about 67/33, about 66/34, about 65/35, about 64/36, about 63/37, about 62/38, about 61/39, or about 60/40, where all ratios are given by weight.

D—Preparation of Inventive Composites by Supercritical Fluid Treatment

As already mentioned above, porous composites of the present invention may be prepared using any of a variety of methods. In certain embodiments, composites described herein are prepared using a method that involves a supercritical fluid. As used herein, the term "supercritical fluid treatment" refers to a process that is conducted in the presence of a supercritical fluid. In many embodiments of the present invention, the process includes contacting the polymer/particles mixture with the supercritical fluid for a certain amount of time and returning supercritical fluid to a non-supercritical state. The supercritical fluid may be returned to a non-supercritical state by reducing its pressure and/or its temperature. In certain embodiments, the supercritical fluid is returned to a non-supercritical state by rapid decompression, i.e., by reducing its pressure in a very short amount of time (e.g., by rapid or explosive decompression). In certain preferred embodiments, of the invention, the supercritical fluid treatment is performed in the presence of supercritical carbon dioxide ($SCCO_2$).

In certain embodiments, desired amounts of the polymer/particles mixture are placed in open metal (e.g., stainless steel) carriers. For example, the mixture may be loaded into the carriers using a vacuum loader, such as those commercially available from Vector Technologies, Ltd. (Milwaukee, Wis.) or Sterling (New Berlin, Wis.). Such a machine draws a pre-determined quantity of the mixture into a small chamber using vacuum and ejects the material into the carrier using a positive pressure. In certain embodiments, the material (i.e., the polymer/particles mixture) is slightly compacted into the carrier using a packing tool. Packing tools can be used that pack the material in the container to a known displacement level within the container, as a way to control packing.

Filled open stainless steel carriers can then be placed into a $SCCO_2$ high pressure chamber or vessel and submitted to a pressure/heating process. For example, the carriers may be placed on a hold rack and the hold rack containing the filled carriers may be loaded in the high pressure vessel. In certain embodiments, at the time of loading the temperature of the pressure vessel is between about room temperature and about 80° C., for example 70° C. The loaded pressure vessel is then purged of atmosphere using gaseous $CO_2$, for example gaseous $CO_2$ at approximately 700 psi. The $SCCO_2$ vessel is pressurized while the temperature of the vessel is ramped up. The temperature of the vessel may be increased in a controlled manner, e.g., at a rate of 3.5° C. per minute. The containers are held at high pressure, for example between 2500 and 10,000 psi, e.g., about 5000 psi to about 8000 psi, for a period of time, e.g., one hour or less (e.g., 30 minutes) at elevated temperature, e.g., between 31.1° C. and 200° C., for example 105° C. or 115° C., in the $SCCO_2$ chamber. The vessel temperature is allowed to fall to below 100° C., for example, to about 90° C., following which the pressure is released rapidly, e.g., from about 6000 psi to atmospheric pressure in about 20 to about 90 seconds, e.g., 75 seconds. The product can then be removed from the $SCCO_2$ vessel and ejected from carriers.

This process fuses the particles and polymer together and introduces porosity into the composite. For a general discussion of the use of porosity in osteoimplants, see U.S. Pat. Appln. No. US 2005-0251267, published Nov. 10, 2005; which is incorporated herein by reference. A porous composite osteoimplant with an interconnecting network of pores has been shown to facilitate the invasion of cells and promote the organized growth of incoming cells and tissue (e.g., living bone) (see, for example, Allcock et al., Macromolecules, 1977, 10: 824-830; Allcock et al., Inorg. Chem., 1982, 21: 515-521; Mikos et al., Proc. ACS Div. of Polymer Mater., 1992, 66: 33; Eggli et al., Clin. Orthop. 1987, 232: 127-138; each of which is incorporated herein by reference). Porosity has also been shown to influence the biocompatibility and bony integration of polymeric composites (White et al., Dental Clinical of N. Amer., 1986, 30: 49-67, which is incorporated herein by reference).

This porosity may include both open and closed cells. The terms "open cells" and "open-celled structure" are used herein interchangeably and refer to a porous material with very large permeability, and where no significant surface barriers exist between cells (i.e., where the pores are connected). The terms "closed cells" and "close-celled structure" are used herein interchangeably and refer to a porous material where the pores are not connected, resulting in a weakly permeable material. Open cells in an inventive composite increase the paths for tissue to infiltrate the composite and will decrease degradation times. The proportion and size distribution ranges of open and closed cells of the final composite may be adjusted by controlling such factors as the time and temperature of supercritical processing, the amount of cooling permitted before the $SCCO_2$ vessel is vented, the speed with which the pressure in the vessel is reduced, the mechanical properties of the polymer, and the proportions of particles and/or polymer in the mixture used to prepare the composite.

Composites of the present invention can exhibit high degrees of porosity over a wide range of effective pore sizes. Thus, composites of the present invention may have, at once, macroporosity, mesoporosity, and microporosity. Macroporosity is characterized by pore diameters greater than about 100 microns. Mesoporosity is characterized by pore diameters between about 100 microns about 10 microns; and microporosity occurs when pores have diameters below about 10 microns. In some embodiments, the composite has a porosity of at least about 5% to about at least 90%. For example, in certain embodiments, the composite has a porosity of more than about 10%, more than about 20%, more than about 30%, more than about 40%, more than about 50%, more than about 60%, more than about 70%, more than bout 80%, or more than about 90%. Advantages of a highly porous composite over less porous or non-porous composite include, but are not limited to, more extensive cellular and tissue ingrowth into the composite, more continuous supply of nutrients, more thorough infiltration of therapeutics, and enhanced revascularization, allowing bone growth and repair to take place more efficiently. Furthermore, the porosity may be loaded with biologically active agents such as drugs, small molecules, cells, peptides, vectors, growth factors, osteoinduction factors, etc, for delivery at the implant site (as described below in more detail). Porosity may also render certain composites of the present invention compressible.

In certain embodiments of the present invention, the pores of the composite are preferably over 100 microns wide for the invasion of cells and bony in-growth (Klaitwatter et al., J. Biomed. Mater. Res. Symp., 1971, 2: 161, which is incorporated herein by reference. In certain embodiments, the pore size ranges from approximately 50 microns to approximately 500 microns, preferably from 100 microns to approximately 250 microns.

In certain embodiments, porous composites of the present invention have a density of between about 1.6 $g/cm^3$ to about 0.02 $g/cm^3$. For example, the density may be between about 1.1 $g/cm^3$ and about 0.05 $g/cm^3$, or between about 0.8 $g/cm^3$ and about 0.07 $g/cm^3$, e.g., less than about 0.8 $g/cm^3$, less than about 0.7 $g/cm^3$, less than about 0.6 $g/cm^3$, less than about 0.5 $g/cm^3$, less than about 0.4 $g/cm^3$, less than about 0.3 $g/cm^3$, less than about 0.2 $g/cm^3$, or less than about 0.1 $g/cm^3$.

Without being bound to any particular theory, it is thought that supercritical processing may also facilitate sterilization of the composite by rendering certain organisms inactive during exposure to supercritical carbon dioxide or during the rapid/explosive decompression at the end of the process. Also, without being bound to any particular theory, it is thought that the supercritical carbon dioxide also removes residual monomer lipids from bone and other components of the mixture that it can permeate or dissolve. Where it is desirable to solubilize materials that are not soluble in supercritical carbon dioxide, other materials, such as ethylene, propylene, ethane, propane, ethanol, propanol, acetone, 1,1, 1,2-tetrafluoroethane, difluoromethane, and pentafluoroethane, in which the desired material is more soluble may be used. These solvents may be combined with the carbon dioxide or used alone. In certain embodiments, $CO_2$ is used alone without other solvents in the process of the material.

Because the composite expands in volume during the rapid pressure release, the shape of the resulting osteoimplant may be controlled by adjusting the shape of the container. For example, if the preformed or blended material is semi-constrained within a bowl-shaped container, the finished composite will take a roughly hemispherical shape. A variety of shapes may be produced using containers that are closed at one end and are filled when the material expands upon the release of pressure. A multi-piece container may be used to produce shapes having complicated cross-sections. Alternatively or additionally, containers having pliable and rigid sections may be used to achieve different levels of porosity within the same product.

Where the composite will be morselized (see below) and the shape of the composite after supercritical treatment is not critical, a bag or other soft or semi-soft container that is permeable to carbon dioxide may be used as the containment vessel. For example, the use of sealed Tyvek® pouches may facilitate mixing of the polymer and particles without leaking, before being placed in the high pressure vessel.

The upper portion of the composite may also be shaped during supercritical treatment by providing an appropriately contoured lid. For example, a concave lid may be used. The lid may be constructed so that carbon dioxide has access to the material inside the container. Upon venting, the lid would contain the bulk of the expanded material, providing the desired shape on the upper surface of the composite. Any flash may be trimmed, for example, using a scalpel. Screens and/or semi-permeable membranes may be employed to define a shape, allow the carbon dioxide to fill the containment chamber, and contain the composite upon expansion.

In some embodiments, composites may be produced with regional variations in composition. For example, bone or other particles and polymer particles may be layered in the container rather than mixed together, and optionally tabletted. Supercritical processing would fuse the particles together, but the composite would have a gradient in particle/polymer ratio from top to bottom. Alternatively or additionally, biologically active agents may be layered in between polymer or particles layers. Polymer screens or other partitions may be used to create sectioned composites.

The overall mechanical strength of a composite material according to the present invention may be augmented by including monolithic bone pieces and/or one or more than one ingot of metal or polymer in the container with the mixture. This fills a structural function for the composite that may allow load-bearing while maintaining the porous structure of the remainder of the composite.

The composite may be used as a coating material on orthopedic implants such as hip prostheses to improve integration of the implant with the patient's bone. Both porous stems and smooth stems may be coated. In one embodiment, a prosthesis with a porous coated stem (e.g., porous metal coating) is put in a bag or rigid container with the particle/polymer mixture. The supercritical treatment solubilizes the polymer and carries it into the pores. Excess material will form a layer extended beyond the pores. Where a rigid container is used, it may be shaped to support the prosthesis and provide a coating having a defined contour.

Alternatively, the porous composite can be applied to the surface of the prosthetic device using any one of several other ways. Thus, e.g., the composite and/or the surface of the prosthesis can be provided with a suitable cement or adhesive such as any of those known in the art, e.g., cyanoacrylate, silicones, hot melt adhesives, cellulosic binders, with subsequent contact of the composite with the prosthesis, e.g., by spraying, brushing, etc., being sufficient to adhere the composite to the surface of the prosthesis or any preselected area(s) or portion(s) of the surface. Another useful procedure involves applying a charge to the prosthesis and an opposite charge to the composite, i.e., using the technique of electrostatic precipitation, with the result that the composite is attracted to, and tenaciously adheres to, the surface of the prosthesis. Any of these application techniques can be repeated one or more times to build up a relatively thick layer of adherent composite on the surface of the prosthesis.

One skilled in the art will recognize that standard experimental techniques may be used to test the properties for a range of compositions and/or supercritical treatment conditions to optimize a composite for a desired application. For example, standard mechanical testing instruments may be used to test the compressive strength and stiffness of the composite. Cells may be cultured on the composite for an appropriate period of time and the metabolic products and the amount of proliferation (e.g., the number of cells in comparison to the number of cells seeded) analyzed. The weight change of the composite may be measured after incubation in saline or other fluids. Repeated analysis will demonstrate whether degradation of the composite is linear or not, and mechanical testing of the incubated material will show the change in mechanical properties as the composite degrades. Such testing may also be used to compare the enzymatic and non-enzymatic degradation of the composite and to determine the levels of enzymatic degradation.

The supercritical processing techniques described herein may also be used for extraction. For example, bone or another material may be treated to remove undesirable materials that are soluble in a first supercritical fluid. Chemical derivatives of the desired product may then be formed, which derivatives would be soluble in the same fluid.

E—Processing of Inventive Composites

Composites of the present invention may be prepared into a specific shape (as described above) or prepared and then formed into the desired shape. Exemplary shapes include, but are not limited to, morsels, block, sheet, plate, particle, sphere, strand, coiled strand, capillary network, film, fiber, mesh, disk, cone, rod, cup, pin, screw, tube, bone or portion of bone, wedge or portion of wedge, cylinder, and threaded cylinder.

In certain embodiments, the composite is morselized to smaller sizes, for example to about 4 mm or less. Alternatively, the composite may be trimmed to form a cylinder, block, wedge, sheet or disk. In other embodiments, the composite is cut into particles having specific shapes, for example, blocks, spheres, etc. The open stainless container used in the supercritical treatment provides a naturally cylindrical shape to the composite, and the diameter may be adjusted to provide a desired size composite block. The product may be shaped using any of a wide variety of means. For example, the product may be shaped with a scalpel, scissors, hand saw, motorized/powered saw, rotary tool, such as Midas Rex® drill systems commercially available from Midas Rex Pneumatic Tools, Inc. (Fort Worth, Tex.), or any other manually operated implement. This may be done to form a specific shape for packaging and sale or by a surgeon just prior to implantation. In some embodiments, the shape may be modified manually just prior to implantation.

The composite may be dried before packaging and sterilization. Non-PEG containing composites may be treated in a vacuum oven at about 80° C. for about 2 hours; PEG-containing implants may be treated at a lower temperature, e.g., less than 50° C. The composite may be packaged in a dry, inert atmosphere, e.g., nitrogen or argon, and sterilized with gamma radiation, e.g., at 2.5-3.5 MRad. Dry ice may be used to keep the material cool during sterilization.

F—Additional Components

The composites of the present invention are useful as stand alone materials, but they can also comprise or be combined with other materials or substances, the presence of which modifies the composite's properties. Thus, one of the advantages of the inventive composites lies in their ability to function as a carrier for, and effectively incorporate, one or more useful substances. These substances can be biologically active or non-biologically active compounds. These substances may be added to the polymer/particles mixture prior to the supercritical carbon dioxide treatment, attached (covalently or non-covalently) to particles and/or polymer prior to the supercritical treatment, or may be incorporated after formation of the composite. The substances may be associated with the composite through specific or non-specific interaction, or covalent or non-covalent interactions. Examples of specific interactions include those between a ligand and a receptor, an epitope and an antibody, etc. Examples of non-covalent interactions include hydrophobic interactions, electrostatic interactions, magnetic interactions, dipole interactions, van der Waals interactions, hydrogen bonding, etc. As will be recognized by one skilled in the art, a composite of the present invention may contain one or more than one substance; and the different substances may be incorporated into the composite using similar or different methods and associated with the composite through similar or different kinds of interactions.

Additional components of the composite may be any type of chemical compound including proteins, peptides, polynucleotides (e.g., vectors, plasmids, cosmids, artificial chromosomes, etc.), lipids, carbohydrates, organic molecules, small molecules, organometallic compounds, metals, inorganic materials, polymers, etc. Living cells, tissue samples, or viruses may also be added to the inventive composites. In certain embodiments, the additional material comprises cells, which may optionally be genetically engineered. For example, the cells may be engineered to produce a specific growth factor, chemotactic factor, osteogenic factor, etc. In certain embodiments, the cells may be engineered to produce a polynucleotide such as an siRNA, shRNA, RNAi, microRNA, etc. The cell may include a plasmid, or other extra-chromosomal piece of DNA. In certain embodiments, a recombinant construct is integrated into the genome of the cell. In certain embodiments, the additional material comprises a virus. Again, the virus may be genetically engineered. Tissues such as bone marrow and bone samples may be combined with the composite of polymer and bone-derived particles. The composite may include additional calcium-based ceramics such as calcium phosphate and calcium carbonate. In certain embodiments, non-biologically active materials are incorporated into the composite. For example, labeling agents such as radiopaque, luminescent, or magnetically active particles may be attached to the bone-derived particles using silane chemistry or other coupling agents, for example zirconates and titanates, or mixed into the polymer, as described herein. Alternatively, or in addition, poly(ethylene glycol) (PEG) may be attached to the bone particles. Biologically active molecules, for example, small molecules, bioactive agents, and biomolecules such as lipids may be linked to the particles through silane SAMs or using a polysialic acid linker (see, for example, U.S. Pat. No. 5,846,951; which is incorporated herein by reference).

In certain embodiments, the composite includes one or more plasticizers. Plasticizers are typically compounds added to polymers or plastics to soften them or make them more pliable. Plasticizers soften, make workable, or otherwise improve the handling properties of a polymer or composite. Plasticizers also allow the inventive composite to be moldable at a lower temperature, thereby avoiding heat induced tissue necrosis during implantation. The plasticizer may evaporate or otherwise diffuse out of the composite over time, thereby allowing the composite to harden or set. Plasticizer are thought to work by embedding themselves between the chains of polymers. This forces the polymer chains apart and thus lowers the glass transition temperature of the polymer. Typically, the more plasticizer that is added, the more flexible the resulting polymer or composite will be. In certain embodiments, the plasticizer is based on an ester of a polycarboxylic acid with linear or branched aliphatic alcohols of moderate chain length. For example, some plasticizers are adipate-based. Examples of adipate-based plasticizers include bis(2-ethylhexyl)adipate (DOA), dimethyl adipate (DMAD), monomethyl adipate (MMAD), and dioctyl adipate (DOA). Other plasticizers are based on maleates, sebacates, or citrates such as bibutyl maleate (DBM), diisobutylmaleate (DIBM), dibutyl sebacate (DBS), triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC), and trimethylcitrate (TMC). Other plasticizers are phthalate based. Examples of phthalate-based plasticizers are N-methyl phthalate, bis(2-ethylhexyl) phthalate (DEHP), diisononyl phthalate (DINP), bis(n-butyl)phthalate (DBP), butyl benzyl phthalate (BBzP), diisodecyl phthalate (DOP), diethyl phthalate (DEP), diisobutyl phthalate (DIBP), and di-n-hexyl phthalate. Other suitable plasticizers include liquid polyhydroxy compounds such as glycerol, polyethylene glycol (PEG), triethylene glycol, sorbitol, monacetin, diacetin, and mixtures thereof. Other plasticizers include trimellitates (e.g., trimethyl trimellitate (TMTM), tri-(2-ethylhexyl) trimellitate (TEHTM-MG), tri-(n-octyl,n-decyl) trimellitate (ATM), tri-(heptyl,nonyl) trimellitate (LTM), n-octyl trimellitate (OTM)), benzoates, epoxidized vegetable oils, sulfonamides (e.g., N-ethyl toluene sulfonamide (ETSA), N-(2-hydroxypropyl)benzene sulfonamide (HP BSA), N-(n-butyl) butyl sulfonamide (BBSA-NBBS)), organophosphates (e.g., tricresyl phosphate (TCP), tributyl phosphate (TBP)), glycols/polyethers (e.g., triethylene glycol dihexanoate, tetraethylene glycol diheptanoate), and polymeric plasticizers. Other plasticizers are described in Handbook of Plasticizers (G. Wypych, Ed., ChemTec Publishing, 2004), which is incorporated herein by reference. In certain embodiments, other polymers are added to the composite as plasticizers. In certain particular embodiments, polymers with the same chemical structure as those used in the composite are used but with lower molecular weights to soften the overall composite. In other embodiments, different polymers with lower melting points and/or lower viscosities than those of the polymer component of the composite are used. In certain embodiments, the polymer used as plasticizer is poly(ethylene glycol) (PEG). The PEG used as a plasticizer is typically a low molecular weight PEG such as those having an average molecular weight of 1000 to 10000 g/mol, preferably from 4000 to 8000 g/mol. In certain embodiments, PEG 4000 is used in the composite. In certain embodiments, PEG 5000 is used in the composite. In certain embodiments, PEG 6000 is used in the composite. In certain embodiments, PEG 7000 is used in the composite. In certain embodiments, PEG 8000 is used in the composite. The plasticizer (PEG) is particularly useful in making more moldable composites that include poly(lactide), poly(D,L-lactide), poly(lactide-co-glycolide), poly(D,L-lactide-co-glycolide), or poly(caprolactone). Plasticizer may comprise 1-40% of the composite by weight. In certain embodiments, the plasticizer is 10-30% by weight. In certain embodiments, the plasticizer is approximately 10% by weight. In certain embodiments, the plasticizer is approximately 15% by weight. In certain embodiments, the plasticizer is approximately 20% by weight. In certain embodiments, the plasticizer is approximately 25% by weight. In certain embodiments, the plasticizer is approximately 30% by weight. In certain embodiments, the plasticizer is approximately 33% by weight. In certain embodiments, the plasticizer is approximately 40% by weight. In certain embodiments, a plasticizer is not used in the composite. For example, in some polycaprolactone-containing composites, a plasticizer is not used.

In certain embodiments, the composite may include a wetting or lubricating agent. Suitable wetting agents include water, organic protic solvents, aqueous solutions such as physiological saline, concentrated saline solutions, sugar solutions, ionic solutions of any kind, and liquid polyhydroxy compounds such as glycerol, polyethylene glycol (PEG), polyvinyl alcohol (PVA), and glycerol esters, and mixtures of any of these. Biological fluids may also be used as wetting or lubricating agents. Examples of biological fluids that may be used with the inventive composites include blood, lymph, plasma, serum, or marrow. Lubricating agents may include, for example, polyethylene glycol, which can be combined with the polymer and other components to reduce viscosity or even coated on the walls of the delivery device. Alternatively or in addition, the particulate material may be coated with a polymer by sputtering or other techniques known to those skilled in the art.

In certain embodiments, the polymer/particle mixture may include polyethylene glycol (PEG). For example, PEG may be added in such a quantity that the final mixture comprises, by weight, at least about 1%, at least about 2%, at least about 3%, at least about 4%, at least about 5%, at least about 6%, or at least about 7% of PEG, or more than 7% PEG. Alternatively or additionally, the polymer itself and/or the particles may be PEGylated, or PEG-oligomer chains may be included in the polymer/particles mixture. PEG and other hydrophilic materials can promote fluid uptake into the finished composite after implantation, allowing easy loading of the composites with blood or cells.

The porosity of the composite may be accomplished using any means known in the art. Exemplary methods of creating porosity in a composite include, but are not limited to, particular leaching processes, gas foaming processing, supercritical carbon dioxide processing, sintering, phase transformation, freeze-drying, cross-linking, molding, porogen melting, polymerization, melt-blowing, and salt fusion (Murphy et al. *Tissue Engineering* 8(1):43-52, 2002; incorporated herein by reference). For a review, see Karageorgiou et al., *Biomaterials* 26:5474-5491, 2005; incorporated herein by reference. The porosity may be a feature of the composite during manufacture or before implantation, or the porosity may only be available after implantation. For example, the implanted composite may include latent pores. These latent pores may arise from including porogens in the composite.

The porogen may be any chemical compound that will reserve a space within the composite while the composite is being molded and will diffuse, dissolve, and/or degrade prior to or after implantation leaving a pore in the composite. Porogens preferably have the property of not being appreciably changed in shape and/or size during the procedure to make the composite moldable. For example, the porogen should retain its shape during the heating of the composite to make it moldable. Therefore, the porogen preferably does not melt upon heating of the composite to make it moldable. In certain embodiments, the porogen has a melting point greater than about 60° C., greater than about 70° C., greater than about 80° C., greater than about 85° C., or greater than about 90° C.

Porogens may be of any shape or size. The porogen may be spheroidal, cuboidal, rectangular, elonganted, tubular, fibrous, disc-shaped, platelet-shaped, polygonal, etc. In certain embodiments, the porogen is granular with a diameter ranging from approximately 100 microns to approximately 800 microns. In certain embodiments, the porogen is elongated, tubular, or fibrous. Such porogens provide increased connectivity of the pores of the composite and/or also allow for a lesser percentage of the porogen in the composite. The amount of the porogen may vary in the composite from 1% to 80% by weight. In certain embodiments, the plasticizer makes up from about 5% to about 80% by weight of the composite. In certain embodiments, the plasticizer makes up from about 10% to about 50% by weight of the composite. Pores in the composite are thought to improve the osteoinductivity or osteoconductivity of the composite by providing holes for cells such as osteoblasts, osteoclasts, fibroblasts, cells of the osteoblast lineage, stem cells, etc. The pores provide the composite with biological in growth capacity. Pores in the composite may also provide for easier degradation of the composite as bone is formed and/or remodeled. Preferably, the porogen is biocompatible.

The porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). The gaseous or liquid porogen may diffuse out of the osteoimplant before or after implantation thereby providing pores for biological in-growth. Solid porogens may be crystalline or amorphous. Examples of possible solid porogens include water soluble compounds. In certain embodiments, the water soluble compound has a solubility of greater than 10 g per 100 mL water at 25° C. In certain embodiments, the water soluble compound has a solubility of greater than 25 g per 100 mL water at 25° C. In certain embodiments, the water soluble compound has a solubility of greater than 50 g per 100 mL water at 25° C. In certain embodiments, the water soluble compound has a solubility of greater than 75 g per 100 mL water at 25° C. In certain embodiments, the water soluble compound has a solubility of greater than 100 g per 100 mL water at 25° C. Examples of porogens include carbohydrates (e.g., sorbitol, dextran (poly(dextrose)), starch), salts, sugar alcohols, natural polymers, synthetic polymers, and small molecules.

In certain embodiments, carbohydrates are used as porogens in the inventive composites. The carbohydrate may be a monosaccharide, disaccharide, or polysaccharide. The carbohydrate may be a natural or synthetic carbohydrate. Preferably, the carbohydrate is a biocompatible, biodegradable carbohydrate. In certain embodiments, the carbohydrate is a polysaccharide. Exemplary polysaccharides include cellulose, starch, amylose, dextran, poly(dextrose), glycogen, etc. In certain embodiments, the polysaccharide is dextran. Very high molecular weight dextran has been found particularly useful as a porogen. For example, the molecular weight of the dextran may range from about 500,000 g/mol to about 10,000,000 g/mol, preferably from about 1,000,000 g/mol to about 3,000,000 g/mol. In certain embodiments, the dextran has a molecular weight of approximately 2,000,000 g/mol. Dextrans with a molecular weight higher than 10,000,000 g/mol may also be used as porogens. Dextran may be used in any form (e.g., particles, granules, fibers, elongated fibers) as a porogen. In certain embodiments, fibers or elongated fibers of dextran are used as the porogen in the inventive composite. Fibers of dextran may be formed using any known method including extrusion and precipitation. Fibers may be prepared by precipitation by adding an aqueous solution of dextran (e.g., 5-25% dextran) to a less polar solvent such as a 90-100% alcohol (e.g., ethanol) solution. The dextran precipitates out in fibers that are particularly useful as porogens in the inventive composite. Dextran may be about 15% by weight to about 30% by weight of the composite. In certain embodiments, dextran is about 15% by weight, 20% by weight, 25% by weight, or 30% by weight. Higher and lower percentages of dextran may also be used. Once the composite with the dextran as a porogen is implanted into a subject, the dextran dissolves away very quickly. Within approximately 24 hours, substantially all of the dextran is out of the composite leaving behind pores in the osteoimplant composite. An advantage of using dextran in the composite is that dextran exhibits a hemostatic property in the extravascular space. Therefore, dextran in a composite can decrease bleeding at or near the site of implantation.

Small molecules including pharmaceutical agents may also be used as porogens in the inventive composites. Examples of polymers that may be used as plasticizers include poly(vinyl pyrollidone), pullulan, poly(glycolide), poly(lactide), and poly(lactide-co-glycolide). Typically low molecular weight polymers are used as porogens. In certain embodiments, the porogen is poly(vinyl pyrrolidone) or a derivative thereof. Plasticizers that are removed faster than the surrounding composite can also be considered porogens.

In certain embodiments, the composite may include a wetting or lubricating agent. Suitable wetting agents include water, organic protic solvents, organic non-protic solvents, aqueous solutions such as physiological saline, concentrated saline solutions, sugar solutions, ionic solutions of any kind, and liquid polyhydroxy compounds such as glycerol, polyethylene glycol (PEG), polyvinyl alcohol (PVA), and glycerol esters, and mixtures of any of these. Biological fluids may also be used as wetting or lubricating agents. Examples of biological fluids that may be used with the inventive composites include blood, lymph, plasma, serum, or marrow. Lubricating agents may include, for example, polyethylene glycol, which can be combined with the polymer and other components to reduce viscosity or even coated on the walls of the delivery device. Alternatively or in addition, the particulate material may be coated with a polymer by sputtering or other techniques known to those skilled in the art.

Alternatively or additionally, the composites may include additional calcium-based materials such as calcium phosphate and calcium carbonate. Non-biologically active materials may also be incorporated into the composite. For example, labeling agents such as radio-opaque, luminescent, or magnetically active particles may be attached to the bone particles using silane chemistry or other coupling agents, for example zirconates and titanates, or mixed with the polymer. As the bone is resorbed, these non-biodegradable materials are removed from the tissue site by natural metabolic processes, allowing the degradation of the composite to be tracked using standard medical diagnostic techniques. The composites of the present invention may further contain other materials such as fillers to improve the strength of the polymer matrix, anti-degradants such as anti-oxidants and anti-ozonants, colorants, chromophores, or any other material that may impart a desired property to the composites.

Alternatively or additionally, composites of the present invention may contain one or more biologically active molecules, including biomolecules, small molecules, and bioactive agents, to promote bone growth and connective tissue regeneration, and/or to accelerate healing. Examples of materials that can be incorporated include chemotactic factors, angiogenic factors, bone cell inducers and stimulators, including the general class of cytokines such as the TGF-β superfamily of bone growth factors, the family of bone morphogenic proteins, osteoinductors, and/or bone marrow or bone forming precursor cells, isolated using standard techniques. Sources and amounts of such materials that can be included are known to those skilled in the art.

To enhance biodegradation in vivo, the composites of the present invention can also include different enzymes. Examples of suitable enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

Composites of the present invention may, alternatively or additionally, be used to deliver other pharmaceutical agents. For example, suitable biologically active agents include substances useful in preventing infection at the implant site, as for example, antiviral, antibacterial, antiparasitic, antifungal substances, and combinations thereof. Other suitable agents include substances capable of acting as a stimulant, sedative, hypnotic analgesic, anticonvulsant, and the like. Other examples of suitable pharmaceutical agents include, but are not limited to, drugs that act at synaptic and neuroeffector junctional sites, drugs that can act on the central nervous system, drugs that can modulate inflammatory responses, antibiotics, anti-cancer agents, immunomodulatory agents, drugs acting on the blood and/or the blood-forming organs, hormones, hormones antagonists, agents affecting calcification and bone turnover, vitamins, gene therapy agents (e.g., viral vectors, nucleic acid-bearing liposomes, DNA-protein conjugates, anti-sense agents), other agents such as targeting agents, etc. RNAi or other similar technologies may be used to reduce the production of various factors.

Examples of bioactive agents that can be delivered using the inventive composites include, but are not limited to, non-collagenous proteins such as osteopontin, osteonectin, bone sialo proteins, fibronectin, laminin, fibrinogen, vitronectin, trombospondin, proteoglycans, decorin, proteoglycans, beta-glycan, biglycan, aggrecan, veriscan, tanascin, matrix gla protein hyaluran, cells; amino acids; peptides; inorganic elements; inorganic compounds; organometallic compounds; cofactors for protein synthesis; cofactors for enzymes; vitamins; hormones; soluble and insoluble components of the immune system; soluble and insoluble receptors including truncated forms; soluble, insoluble, and cell surface bound ligands including truncated forms; chemokines, interleukines; antigens; bioactive compounds that are endocytozed; tissue or tissue fragments; endocrine tissue; enzymes such as collagenase, peptidases, oxidases, etc; polymeric cell scaffolds with parenchymal cells; angiogenic drugs, polymeric carriers containing bioactive agents; encapsulated bioactive agents; bioactive agents in time-release form; collagen lattices, antigenic agents; cytoskeletal agents; cartilage fragments; living cells such as chondrocytes, osteoblasts, osteoclasts, fibroclasts, bone marrow cells, mesenchymal stem cells, etc; tissue transplants; bioadhesives; bone morphogenic proteins (BMPs), transforming growth factors (TGF-β), insulin-like growth factor, platelet derived growth factor (PDGF); fibroblast growth factors (FGF), vascular endothelial growth factors (VEGF), epidermal growth factor (EGF), growth factor binding proteins, e.g., insulin-like growth factors; angiogenic agents; bone promoters; cytokines; interleukins; genetic material; genes encoding bone promoting action; cells containing genes encoding bone promoting action; cells genetically altered by the hand of man; externally expanded autograft or xenograft cells; growth hormones such as somatotropin; bone digestors; anti-tumor agents; fibronectin; cellular attractants and attachment agents; immunosuppressants; bone resorption inhibitors and stimulators; mitogenic factors; bioactive factors that inhibit and stimulate second messenger molecules; cell adhesion molecules, e.g., cell-matrix and cell-cell adhesion molecules; secondary messengers; monoclonal antibodies specific to cell surface determinants on mesenchymal stem cells; portions of monoclonal antibodies specific to cell surface determinants on mesenchymal stem cells; portions of monoclonal antibodies specific to cell surface determinants on mesenchymal stem cells; clotting factors; polynucleotides; and combinations thereof. The amount of bioactive agent included in the composite can vary widely and will depend on such factors as the agent being delivered, the site of administration, the patient's physiological condition, etc. The optimum levels will be determined in a specific case based upon the intended use of the implant.

Preferably, the sites where the biologically active or non-biologically active agents are attached to in the composite, are biodegradable so that the agents can be release to the adjacent tissue fluids during biodegradation of the composite. In certain embodiments, agents are released into the surrounding tissues at a controlled rate. For example, the polymer matrix may be formulated to degrade after an effective and/or substantial amount of the agent is released from the composite. Release of a substance having a low solubility in water, as for example, a peptide or a protein, may require the degradation of a substantial part of the polymer matrix to expose the agent directly to the surrounding tissue fluids. Thus, the release of the agent from the composite may be dependent on, for example, the solubility of the agent in water, the distribution of the agent within the composite, or the size, shape, porosity, solubility and biodegradability of the composite.

As already mentioned above, in certain embodiments, the substance(s) to be incorporated into the composite is/are added to the polymer/particles mixture prior to the supercritical treatment. Preferably, such substances (or solutions thereof) are either soluble in supercritical carbon dioxide or can be suspended in $SCCO_2$.

In other embodiments, the substance(s) to be incorporated into the composite is/are covalently or non-covalently attached to the polymer and/or to the particles before formation of the composite by supercritical treatment. For example, biologically active or non-biologically active agents can be covalently linked to bone particles before combination with the polymer. Silane coupling agents having amine, carboxyl, hydroxyl, or mercapto groups may be attached to the bone particles through the silane and then to the reactive groups on a biomolecule, small molecule or bioactive agent. An exemplary list of silanes that may be used with the present invention is provided in U.S. Publication No. 2004-0146543, the contents of which are incorporated herein by reference. As will be appreciated by on skilled in the art, the coupling agent may be optimized for the compound being attached to the bone particle. Silanes are commercially available from, for example, Union Carbide, AP Resources Co. (Seoul, South Korea), and BASF. Biomolecules, small molecules or bioactive agents may, alternatively or additionally, be attached to a silane-derivatized polymer. Non-silane linkers may also be employed in the present invention. For example, isocyanates will form covalent bonds with hydroxyl groups on the surface of hydroxyapatite ceramics. Polyamines, organic compounds containing one or more primary, secondary or tertiary amines, will also bind with both the bone particle and many polymer side groups. Polyamines and isocyanates may be obtained from Sigma-Aldrich. If a material, for example a metal atom or cluster, cannot be attached to bone particle through a silane or other coupling agent, then a chelating agent may be immobilized on the bone particle surface and allowed to form a chelate with the atom or cluster.

The collagen fibers exposed by demineralization of bone particles are typically relatively inert but have some exposed amino acid residues that can participate in reactions between the bone and a biologically active or non-biologically active molecule. The collagen fibers may be rendered more reactive by fraying the triple helical structure of the collagen to increase the exposed surface area and the number of exposed amino-acid residues. This not only increases the surface area available for chemical reactions but also for mechanical interaction with the polymer as well. Rinsing the partially demineralized bone particles in an alkaline solution will fray the collagen fibers. For example, bone particles may be suspended in water at a pH of about 10 for about 8 hours, after which the solution is neutralized. One skilled in the art will recognize that the pH, the time period, or both may be adjusted to modify the extent of fraying. Agitation, for example, in an ultrasonic both, may reduce the processing time. Alternatively, the particles may be sonicated with water, surfactant, alcohol, or some combination of these.

Alternatively, the collagen fibers may be cross-linked. A variety of cross-linking techniques suitable for medical applications are well known in the art (see, for example, U.S. Pat. No. 6,123,781, the contents of which are incorporated herein by reference). For example, compounds like 1-ethyl-3-(3-dimethylaminopropyl) carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, Biotechnol. Appl. Biochem., 1993, 17: 23-29; PCT Publication WO 98/19718, the contents of both of which are incorporated herein by reference). Alternatively, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification or carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link the collagen. The bone-derived particles are then washed to remove all leachable traces of the material. Enzymatic cross-linking agents may also be used. Additional cross-linking methods include chemical reaction, irradiation, application of heat, dehydrothermal treatment, enzymatic treatment, etc. One skilled in the art will easily be able to determine the optimal concentrations of cross-linking agents and incubation times for the desired degree of cross-linking.

Both frayed and unfrayed collagen fibers may be derivatized with biomolecules, small molecules, inorganic materials, bioactive molecules, biologically inactive compounds, or some combination of these. These materials may be covalently or non-covalently linked to the exposed collagen strands through reactive amino acids on the collagen fiber such as lysine, arginine, hydroxylysine, proline, and hydroxyproline. Alternatively, or in addition, bone-derived particles may be treated to induce calcium phosphate deposition and crystal formation on exposed collagen fibers. Calcium ion association to the surface provides a biocompatible surface, which allows for the attachment of cells as well as crystal growth. The polymer will interact with these fibers, increasing interfacial area and improving the wet strength of the composite.

Additionally or alternatively, the surface treatments described above or treatments such as etching may be used to increase the surface area or surface roughness of the bone-derived particles. Such treatments increase the interfacial strength of the particle/polymer interface by increasing the surface area of the interface and/or the mechanical interlocking of the bone-derived particles and the polymer. Such surface treatments may also be employed to round the shape or smooth the edges of bone particles to facilitate delivery of the inventive composite. Such treatment is particularly useful for injectable composites.

The biologically or non-biologically active substances may alternatively be added after formation of the composite, for example using standard dip or spray application techniques followed by drying. Alternatively, the composite can be treated with reagents that regenerate functional groups (e.g., on the polymeric matrix) to which biologically or non-biologically active substances can be chemically or physically attached. In certain embodiments, a substance is attached to the composite using a linker so that the substance is free to associate with its receptor or site of action in vivo. In other embodiments, the substance to be delivered is attached to an antibody, of fragments thereof, that recognizes the epitope found within the composite. In addition, the surface of the composite can be submitted to plasma etching or chemical oxidation to render the composite more reactive and increase its affinity for the agent to be attached to it (see, for example, U.S. Pat. Nos. 6,033,582 and 6,119,028, each of which is incorporated herein by reference in its entirety).

The composite may also be seeded with cells. In certain embodiments, a patient's own cells are obtained and used in the inventive composite. Certain types of cells (e.g., osteoblasts, fibroblasts, stem cells, cells of the osteoblast lineage, etc.) may be selected for use in the composite. In other embodiments, a patient's own cells may be harvested, expanded, and used in the inventive composite. Alternatively, exogenous cells may be employed. Exemplary cells for use with the invention include mesenchymal stem cells and connective tissue cells, including osteoblasts, osteoclasts, fibroblasts, preosteoblasts, and partially differentiated cells of the osteoblast lineage. The cells may be genetically engineered. For example, the cells may be engineered to produce a bone morphogenic protein.

G—Osteoimplants

Once a composite of the invention has been shaped into an implant, it can be used as such or further processed. The goal of these further treatments is to modify the properties of the implant, such as its rate of degradation or its ability to promote bone growth, and/or to change the shape of the implant in order to broaden the range of its potential clinical applications.

For example, the surface of the implant can be oxidized using a solvent or gas to break some of the polymer chains and thereby accelerate the initial decomposition of the implant. The implant can also be machined according to techniques well known in the art. For example, a composite shaped as a block can be machined into a desired shape. These machined components may be attached to one another using mechanical fasteners such as dowels, pins and screws, all of which may be fabricated from the composite of the invention. Alternatively or additionally, the machined pieces may be attached to one another, using a biocompatible adhesive or chemical cross-linking agent or using ultrasonic bonding. Biocompatible adhesives include, but are not limited to, biocompatible cyanoacrylates, epoxy-based compounds, dental resin sealants, dental resin cements, glass ionomer cements, poly(methyl methacrylate), gelatin-resorcinol-formaldehyde glues, collagen-based glues, inorganic bonding agents such as zinc phosphate, magnesium phosphate, and other phosphate based cements, zinc carboxylate, and protein-based binders, such as fibrin glues and mussel-derived adhesive proteins.

Alternatively or additionally, the composites of the present invention may be combined with other materials and/or structures, including, but not limited to, allograft rings, and Polyetheretherketone (PEEK) Spacers for Spinal Fusion.

The present invention further provides an osteoimplant at least partially coated with an inventive porous composite. Between about 1% and 100% of the surface of the osteoimplant may be coated with an inventive porous composite, for example, between about 5% and about 20%, between about 10% and about 50%, between about 30% and about 75%, between about 50% and about 90%, between 75% and about 95% or more than 95%, e.g. about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

II—Use of Inventive Porous Composites

Composites of the present invention, which are cohesive without necessarily exhibiting high mechanical strength, may be used in a wide variety of clinical applications. A few examples of potential applications are discussed in more detail below.

For example, a composition of the present invention may be used as a bone void filler. Bone fractures and defects, which result from trauma, injury, infection, malignancy or developmental malformation can be difficult to heal in certain circumstances. If a defect or gap is larger than a certain critical size, natural bone is unable to bridge or fill the defect or gap. These are several deficiencies that may be associated with the presence of a void in a bone. The bone void may compromise the mechanical integrity of the bone, making the bone potentially susceptible to fracture until the void becomes ingrown with native bone. Accordingly, it is of interest to fill such voids with a substance which helps the void to eventually fill with naturally grown bone. Open fractures and defects in practically any bone may be filled with composites according to various embodiments without the need for periosteal flap or other material for retaining the composite in the fracture or defect. Even where the composite is not required to bear weight, physiological forces will tend to encourage remodeling of the composite to a shape reminiscent of the original tissue.

Many orthopedic, periodontal, neurosurgical, oral and maxillofacial surgical procedures require drilling or cutting into bone in order to harvest autologous implants used in the procedures or to create openings for the insertion of implants. In either case voids are created in bones. In addition to all the deficiencies associated with bone void mentioned above, surgically created bone voids may provide an opportunity for incubation and proliferation of any infective agents that are introduced during the surgical procedure. Another common side effect of any surgery is ecchymosis in the surrounding tissues which results from bleeding of the traumatized tissues. Finally, the surgical trauma to the bone and surrounding tissues is known to be a significant source of post-operative pain and inflammation. Surgical bone voids are sometimes filled by the surgeon with autologous bone chips that are generated during trimming of the bony ends of the graft to accommodate graft placement, thus accelerating healing. However, the volume of these chips is typically not sufficient to completely fill the void. Composites of the present invention, for example composites comprising anti-infective and/or anti-inflammatory agents, may be used to fill surgically created bone voids.

The inventive composite may be administered to a subject in need thereof using any technique known in the art. The subject is typically a patient with a disorder or disease related to bone. In certain embodiments, the subject has a bony defect such as a fracture. The subject is typically a mammal although any animal with bones may benefit from treatment with the inventive composite. In certain embodiments, the subject is a vertebrate (e.g., mammals, reptiles, fish, birds, etc.). In certain embodiments, the subject is a human. In other embodiments, the subject is a domesticated animal such as a dog, cat, horse, etc. Any bone disease or disorder may be treated using the inventive composite including genetic diseases, congenital abnormalities, fractures, iatrogenic defects, bone cancer, bone metastases, inflammatory diseases (e.g. rheumatoid arthritis), autoimmune diseases, metabolic diseases, and degenerative bone disease (e.g., osteoarthritis). In certain embodiments, the inventive osteoimplant composites are formulated for the repair of a simple fracture, compound fracture, or non-union; as an external fixation device or internal fixation device; for joint reconstruction, arthrodesis, arthroplasty, or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones, and for repair of bone surrounding cysts and tumors.

Composites of the present invention can be used as bone void fillers either alone or in combination with one or more other conventional devices, for example, to fill the space between a device and bone. Examples of such devices include, but are not limited to, bone fixation plates (e.g., cranofacial, maxillofacial, orthopedic, skeletal, and the like); screws, tacks, clips, staples, nails, pins or rods, anchors (e.g., for suture, bone, and the like), scaffolds, scents, meshes (e.g., rigid, expandable, woven, knitted, weaved, etc), sponges, implants for cell encapsulation or tissue engineering, drug delivery (e.g., carriers, bone ingrowth induction catalysts such as bone morphogenic proteins, growth factors, peptides, antivirals, antibiotics, etc), monofilament or multifilament structures, sheets, coatings, membranes (e.g., porous, microporous, resorbable, etc), foams (e.g., open cell or close cell), screw augmentation, cranial, reconstruction, and/or combinations thereof.

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Mineralized human cortical bone particles (about 200-500 microns), were mixed in a ratio of about 80/20 with RESOMER™ 824 particles ground to about the same size. The mixture was tabletted, and a known number of tablets were placed in a stainless steel cylinder that is closed at one end. The cylinder was then placed in a supercritical $CO_2$ chamber and held at 5000 psi for 1 hour at 115° C. The chamber was allowed to cool to 90° C. and then vented, reaching atmospheric pressure in about 20 seconds. The composite resulting from this process had a porosity of about 60-70%. The wet compressive strength was about 3 MPa at 20% engineering strain but reached 4-5 MPa at higher strains.

Example 2

Composites were prepared as described in Example 1, but with rabbit bone fibers up to about 3 mm long and with a 50/50 ratio of rabbit bone fibers and polymer. After supercritical treatment, samples including about half gram of material had porosities of about 61% and about 52%.

Example 3

Composites were prepared as described in Example, but with a 50/50 ratio of rabbit bone particles and polymer. The mixture was pre-packed dry at a pressure of about 200 psi and treated with supercritical $CO_2$ as in Example 1. Samples of about 0.9 g of the resulting product had a porosity of about 62% and about 77%.

Example 4

Figure 2:
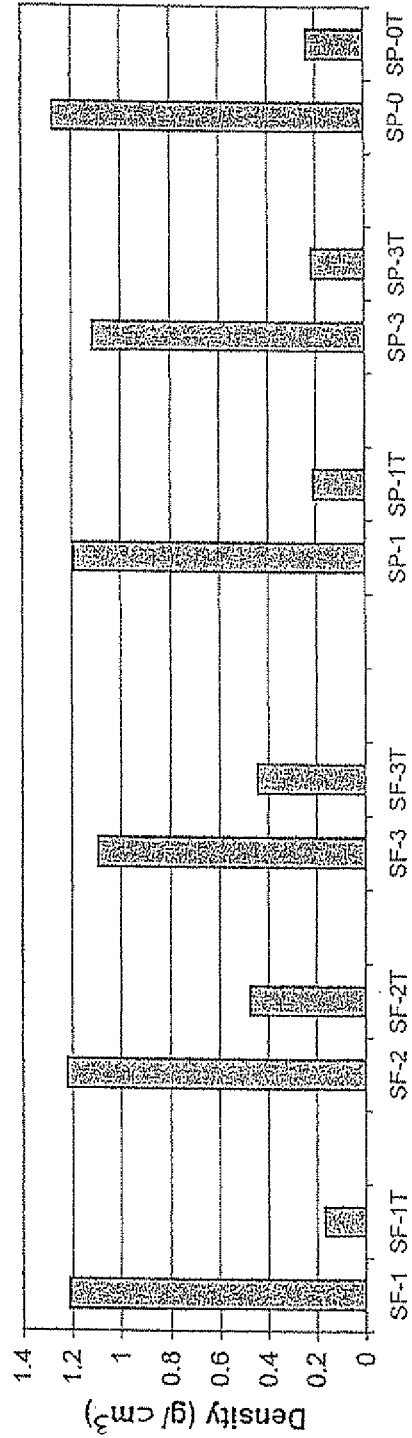
FIG. 2 is a graph comparing the densities of composites according to an embodiment of the invention before and after supercritical treatment.
Figure 4:
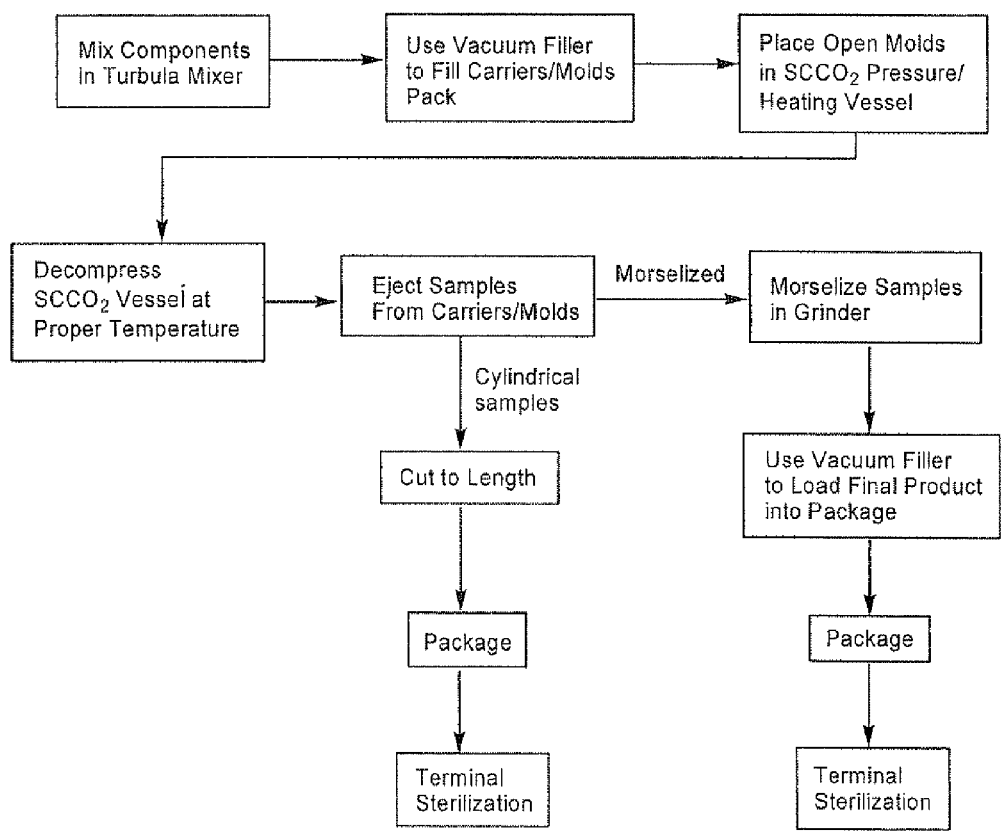
FIG. 4 presents a process diagram for an exemplary method of producing porous composites according to an embodiment of the present invention.

Composites were prepared as described in Example, but with a 50/50 ratio of rabbit bone particles and polymer. Results of a comparison of the material density before and after supercritical treatment are presented in FIG. 2.

Example 5

FIG. 3 is a table comparing the physical properties of composites produced with various combinations of particles and fibers with poly(desamino tyrosyl-tyrosine ethyl ester carbonate) (poly DTE carbonate), RESOMER™ 706, RESOMER™ 824, and polycaprolactone, with or without PEG. The composites were compression molded, molded by hand, or using the supercritical $CO_2$ method as described in Example 1.

Example 6

Femurs from humans or rabbits were debrided and cleaned of marrow, soaked in 70% ethanol, and lavaged with water. Rabbit femurs were frozen into blocks of sterile deionized water to ease milling. All femurs were milled into fibers, which were sonicated in 70% ethanol, lavaged with water, and lyophylized. The fibers were sieved to 300-800 microns, dried in dessicant at 80° C. for 30 minutes, double foil bagged, and stored in a dessicator.

Poly-lactide-co-glycolide was cryoground in a closed container submerged in liquid nitrogen. The particles were sieved to 200-500 microns and dried and stored as above.

Bone fibers and polymer particles were mixed at a ration of 65/35 by weight in a Turbula mixer for 5 minutes. The mixture was fed into a tablet press, which imparts additional mixing, and tabletted. The tablet was incubated in supercritical carbon dioxide at 500 psi for 1 hour at 115° C., cooled to 90° C. under pressure, and then allowed to come to atmospheric pressure quickly (20 to 90 seconds). The resulting product was morselized by hand. The morsels were sieved to between 100 micron and 3 mm and packaged.

Example 7

Bone was prepared as in Example 6. A known weight of polycaprolactone was heated to about 70° C., and a desired amount of bone fibers were added to make a 65/35 ratio of bone to polymer. The mass was folded and lightly pressed to mix the materials while the polymer was still soft, then formed to a desired shape. Cooling solidified the composite, which was then packaged.

Example 8

A composite was prepared that comprises by weight 63% mineralized bone, 32% RESOMER™ 824 (lactide-co-glycolide), and 5% polyethylene glycol (PEG).

Bone particles/fibers were defatted by sonication in 70% ethanol for between 1 and 3 hours. Resulting bone particles were sieved for cross-section dimension (300-800 microns), and the particle lengths were approximately 1-4 mm (i.e., elongated particles or short fibers).

RESOMER™ 824 and PEG were each ground and then sieved to a size range of 200-500 microns. This size range was used in the mixture in the ratios indicated above. All the components were mixed in a complex motion tumbler (TURBULA); and then loaded into cylindrical carriers using a vacuum loader. The vacuum loader draws a known quantity of the material (i.e., particles/polymer mixture) into a small chamber using vacuum, then transfers its into the carrier using positive pressure to eject the material. The material was slightly compacted into the carrier using a packing tool that packs the known amount of material in the carrier to a known displacement level within the carrier. The filled carriers were loaded into a hold rack and the rack was loaded into the $SCCO_2$ pressure/heating vessel at a temperature of 70° C.

After loading, the pressure vessel was purged of atmosphere for about 1 to 2 minutes using gaseous $CO_2$ at approximately 700 psi. The $SCCO_2$ vessel was then pressurized to 500 psi at the 70° C. loading pressure. This pressure was allowed to rise as the temperature was ramped up. Generally, $SCCO_2$ pressure reached a maximum of about 7500 to 8000 psi during the process. The $SCCO_2$ vessel temperature was raised to 105° C. at a rate of 3.5° C./minute. The temperature was controlled and held at 105° C. for 25 minutes. The outer chamber was then opened and the $SCCO_2$ vessel was allowed to cool to 90° C. The chamber was decompressed with the internal SCCO2 temperature reaches 90° C., with pressure venting taking approximately 60-90 seconds.

The product was then removed from SCCO2 vessel and ejected from the carriers. After ejection, cylinders were trimmed to length to give cylindrical final products. Cylindrical products were then vacuum packed in double foil pouches.

Alternatively, after ejection, the entire cylinders were ground in a Quadro mill, then sieved to retrieve 1-4 mm morsel sizes. Morsels were then place in glass vials, in which atmospheric gas was replaced with dry nitrogen. The vials were then sealed under a slight vacuum to prevent stopper from popping out from atmospheric pressure variations. Stoppers were sealed with an aluminum crimp top. The vials were then packaged in a tray with foil lids (outer packaging).

Blocks, wedges, and sheets of the composites could also be made following a process similar to that used to make the cylindrical forms. These shapes can be packaged in foil.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method of making a porous composite comprising steps of:
   providing a plurality of particles comprising a bone-derived material, an inorganic material, a bone substitute material, or any combination thereof;
   providing a biocompatible polymer and a plasticizer comprising poly(ethylene glycol) (PEG); mixing the plurality of particles, the biocompatible polymer, and the plasticizer to obtain a mixture; and
   submitting the mixture to a supercritical fluid treatment that comprises steps of:
      contacting the mixture with a supercritical fluid having a maximum pressure of about 7500 to about 8000 psi, and
      returning the supercritical fluid to a non-supercritical state by rapid or explosive decompression to atmospheric pressure in about 60 seconds to about 90 seconds, so that the porous composite is obtained, the porous composite having a wet compressive strength between about 3 MPa to about 5 MPa and having the PEG in an amount comprising 1-40% by weight of the porous composite.

2. The method of claim 1, wherein the porous composite has a porosity of at least about 30%, at least about 50%, at least about 60%, at least about 70%, at least about 80%, at least about 90% or more than 90%.

3. The method of claim 1, wherein the porous composite, after implantation, has pores or channels that can support the in-growth of cells.

4. The method of claim 1, wherein the bone-derived material is obtained from a member of the group consisting of autologous bone, allogenic bone, xenogenic bone, and mixtures thereof.

5. The method of claim 1, wherein the bone-derived material is obtained from a member of the group consisting of non-demineralized bone particles, demineralized bone particles, deorganified bone particles, partially demineralized bone particles, anorganic bone particles, and combinations thereof.

6. The method of claim 1, wherein the inorganic material or bone substitute material is selected from the group consisting of aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, $\alpha$-tricalcium phosphate, dicalcium phosphate, $\beta$-tricalcium phosphate, tetracalcium phosphate, amorphous calcium phosphate, octacalcium phosphate (OCP), fluoroapatite, chloroapatite, magnesium-substituted tricalcium phosphate, carbonate hydroxyapatite, and combinations and derivative thereof.

7. The method of claim 1, wherein the porous composite further comprises one or more of: inorganic material and a bone-derived material and one or more of bovine serum albumin, collagen, an extracellular matrix component, a synthetic polymer, and a naturally-derived polymer.

8. The method of claim 1, wherein the porous composite comprises approximately 40-70% of the plurality of particles by weight.

9. The method of claim 1, wherein the biocompatible polymer is selected from the group consisting of poly(L-lactide-co-D,L-lactide), polyglyconate, poly(arylates), poly(anhydrides), poly(hydroxy acids), polyesters, poly(ortho esters), poly(alkylene oxides), polycarbonates, poly(propylene fumarates), poly(propylene glycol-co fumaric acid), poly(caprolactones), polyamides, polyesters, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxy-butyrate/valerate copolymers, poly(vinyl pyrrolidone), polycyanoacrylates, poly-urethanes, and polysaccharides.

10. The method of claim 1, wherein the biocompatible polymer comprises poly(caprolactone).

11. The method of claim 1, wherein the biocompatible polymer comprises poly(lactide), poly(glycolide), poly(lactide-co-glycolide), and/or combination thereof.

12. The method of claim 1, wherein the biocompatible polymer is resorbed within approximately 1 month to approximately 3 years.

13. The method of claim 1, wherein the porous composite further comprises a lubricant agent.

14. The method of claim 1, wherein the plasticizer further comprises bis(2-ethylhexyl)adipate (DOA), dimethyl adipate (DMAD), monomethyl adipate (MMAD), dioctyl adipate (DOA, bibutyl maleate (DBM), diisobutylmaleate (DIBM), dibutyl sebacate (DBS), triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC), trimehtylcitrate (TMC), N-methyl phthalate, bis(2-ethylhexyl) phthalate (DEHP), diisononyl phthalate (DINP), bis(n-butyl)phthalate (DBP), butyl benzyl phthalate (BBzP), diisodecyl phthalate (DOP), diethyl phthalate (DEP), diisobutyl phthalate (DIBP), di-n-hexyl phthalate, glycerol, triethylene glycol, sorbitol, monacetin, diacetin, trimethyl trimellitate (TMTM), tri-(2-ethylhexyl) trimellitate (TEHTM-MG), tri-(n-octyl,n-decyl) trimellitate (ATM), tri-(heptyl,nonyl) trimellitate (LTM), n-octyl trimellitate (OTM), benzoates, epoxidized vegetable oils, sulfonamides, N-ethyl toluene sulfonamide (ETSA), N-(2-hydroxypropyl) benzene sulfonamide (HP BSA), N-(n-butyl) butyl sulfonamide (BBSA-NBBS), organophosphates, tricresyl phosphate (TCP), tributyl phosphate (TBP), triethylene glycol dihexanoate, tetraethylene glycol diheptanoate, and polymeric plasticizers.

15. The method of claim 1, wherein the porous composite further comprises a porogen.

16. The method of claim 15, whereby the porogen dissolves and/or degrades after implantation of the porous composite leaving a pore.

17. The method of claim 1, wherein the porous composite further comprises a bioactive agent.

18. The method of claim 17, wherein the bioactive agent is selected from the group consisting of antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, penetration enhancer, anti-inflammatory agents, growth factors, angiogenic factors, antibiotics, analgesics, chemotactic factors, bone morphogenic protein, and cytokines.

19. The method of claim 1, wherein the porous composite further comprises a pharmaceutically acceptable excipient.

20. The method of claim 1, wherein the porous composite has a shape selected from the group consisting of morsels, cylinder, block, wedge, and sheet.

21. The method of claim 1, wherein the plurality of particles and the biocompatible polymer are dried.

22. The method of claim 1, wherein the porous composite comprises at least approximately 50% of the plurality of particles by weight.

23. The method of claim 1, wherein the plurality of particles have a size range of 200-500 microns.

24. The method of claim 1, wherein the biocompatible polymer is ground and sieved to give a particle size range on the same scale as the plurality of particles.

25. The method of claim 1, wherein the porous composite has macroporosity, mesoporosity, and/or microporosity.

26. The method of claim 1, wherein the porous composite has macroporosity, mesoporosity, and microporosity.

27. The method of claim 1 or 25, wherein the porous composite has macroporosity characterized by pore diameters greater than about 100 microns.

28. The method of claim 1, wherein the plasticizer has an average molecular weight of from 4000 to 8000 g/mol.

29. The method of claim 1, wherein the PEG is PEG 6000.

* * * * *